(12) United States Patent
Farritor et al.

(10) Patent No.: US 11,974,824 B2
(45) Date of Patent: May 7, 2024

(54) ROBOTIC SURGICAL DEVICES WITH TRACKING CAMERA TECHNOLOGY AND RELATED SYSTEMS AND METHODS

(71) Applicant: Virtual Incision Corporation, Lincoln, NE (US)

(72) Inventors: Shane Farritor, Lincoln, NE (US); Dmitry Oleynikov, Omaha, NE (US); Nathan Wood, Lincoln, NE (US); Jason Dumpert, Omaha, NE (US); Mark Reichenbach, Lincoln, NE (US); Lou Cubrich, Lincoln, NE (US)

(73) Assignee: Virtual Incision Corporation, Lincoln, NE (US)

( * ) Notice: Subject to any disclaimer, the term of this patent is extended or adjusted under 35 U.S.C. 154(b) by 16 days.

(21) Appl. No.: 17/367,915

(22) Filed: Jul. 6, 2021

(65) Prior Publication Data
US 2021/0330404 A1 Oct. 28, 2021

Related U.S. Application Data

(63) Continuation of application No. 16/144,807, filed on Sep. 27, 2018, now Pat. No. 11,051,894.
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/20* (2016.02); *A61B 34/25* (2016.02); *A61B 90/361* (2016.02);
(Continued)

(58) Field of Classification Search
CPC ......... A61B 34/30; A61B 34/20; A61B 34/25; A61B 90/361; A61B 34/76;
(Continued)

(56) References Cited

U.S. PATENT DOCUMENTS

| 2,858,947 A | 11/1958 | Chapman |
| 3,817,403 A | 6/1974 | Glachet et al. |

(Continued)

FOREIGN PATENT DOCUMENTS

| CA | 2918531 A1 | 1/2015 |
| CN | 102499759 A | 6/2012 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Bhavesh V Amin
(74) *Attorney, Agent, or Firm* — Fredrikson & Byron, P.A.

(57) ABSTRACT

The various inventions relate to robotic surgical devices, consoles for operating such surgical devices, operating theaters in which the various devices can be used, insertion systems for inserting and using the surgical devices, and related methods. A positionable camera is disposed therein, and the system is configured to execute a tracking and positioning algorithm to re-position and re-orient the camera tip.

18 Claims, 19 Drawing Sheets

Related U.S. Application Data

(60) Provisional application No. 62/564,076, filed on Sep. 27, 2017.

(51) Int. Cl.
*A61B 34/20* (2016.01)
*A61B 90/00* (2016.01)

(52) U.S. Cl.
CPC . *A61B 2034/2055* (2016.02); *A61B 2034/302* (2016.02); *A61B 2034/305* (2016.02); *A61B 34/76* (2016.02); *A61B 2090/3614* (2016.02)

(58) Field of Classification Search
CPC ...... A61B 2034/2055; A61B 2034/302; A61B 2034/305; A61B 2090/3614
See application file for complete search history.

(56) References Cited

U.S. PATENT DOCUMENTS

| | | |
|---|---|---|
| 3,870,264 A | 3/1975 | Robinson |
| 3,922,930 A | 12/1975 | Fletcher et al. |
| 3,971,266 A | 7/1976 | Inakura et al. |
| 3,989,952 A | 11/1976 | Timberlake et al. |
| 4,246,661 A | 1/1981 | Pinson |
| 4,258,716 A | 3/1981 | Sutherland |
| 4,278,077 A | 7/1981 | Mizumoto |
| 4,353,677 A | 10/1982 | Susnjara et al. |
| 4,538,594 A | 9/1985 | Boebel et al. |
| 4,568,311 A | 2/1986 | Miyaki |
| 4,576,545 A | 3/1986 | Maeda |
| 4,623,183 A | 11/1986 | Aomori |
| 4,636,138 A | 1/1987 | Gorman |
| 4,645,409 A | 2/1987 | Gorman |
| 4,684,313 A | 8/1987 | Minematsu et al. |
| 4,736,645 A | 4/1988 | Zimmer |
| 4,762,455 A | 8/1988 | Coughlan et al. |
| 4,771,652 A | 9/1988 | Zimmer |
| 4,852,391 A | 8/1989 | Ruch |
| 4,854,808 A | 8/1989 | Bisiach |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,984,959 A | 1/1991 | Kato |
| 4,990,050 A | 2/1991 | Tsuge et al. |
| 5,019,968 A | 5/1991 | Wang et al. |
| 5,036,724 A | 8/1991 | Rosheim |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,372,147 A | 12/1994 | Lathrop et al. |
| 5,382,885 A | 1/1995 | Salcudean et al. |
| 5,441,494 A | 1/1995 | Oritz |
| 5,388,528 A | 2/1995 | Pelrine et al. |
| 5,397,323 A | 3/1995 | Taylor et al. |
| 5,436,542 A | 7/1995 | Petelin et al. |
| 5,456,673 A | 10/1995 | Ziegler et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,667,354 A | 9/1997 | Nakazawa |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,833,656 A | 11/1998 | Smith et al. |
| 5,841,950 A | 11/1998 | Wang et al. |
| 5,845,646 A | 12/1998 | Lemelson |
| 5,855,583 A | 1/1999 | Wang et al. |
| 5,876,325 A * | 3/1999 | Mizuno ............... A61B 34/37 600/117 |
| 5,878,193 A | 3/1999 | Wang et al. |
| 5,878,783 A | 3/1999 | Smart |
| 5,895,377 A | 4/1999 | Smith et al. |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,954,692 A | 9/1999 | Smith et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,106,521 A | 8/2000 | Blewett et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |

(56) References Cited

U.S. PATENT DOCUMENTS

| | | |
|---|---|---|
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,450,992 B1 | 9/2002 | Cassidy |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,826,977 B2 | 12/2004 | Grover et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,793 B2 | 1/2005 | Brock et al. |
| 6,852,107 B2 | 2/2005 | Wang et al. |
| 6,853,879 B2 | 2/2005 | Sunaoshi |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,963,792 B1 | 11/2005 | Green |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 6,999,852 B2 | 2/2006 | Green |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |

(56) References Cited

U.S. PATENT DOCUMENTS

| | | |
|---|---|---|
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,155,316 B2 | 12/2006 | Sutherland et al. |
| 7,163,525 B2 | 1/2007 | Franer |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,403,836 B2 | 7/2008 | Aoyama |
| 7,438,702 B2 | 10/2008 | Hart et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,734,375 B2 | 6/2010 | Buehler et al. |
| 7,762,825 B2 | 7/2010 | Burbank et al. |
| 7,772,796 B2 | 8/2010 | Farritor et al. |
| 7,785,251 B2 | 8/2010 | Wilk |
| 7,785,294 B2 | 8/2010 | Hueil et al. |
| 7,785,333 B2 | 8/2010 | Miyamoto et al. |
| 7,789,825 B2 | 9/2010 | Nobis et al. |
| 7,789,861 B2 | 9/2010 | Franer |
| 7,794,494 B2 | 9/2010 | Sahatjian et al. |
| 7,865,266 B2 | 1/2011 | Moll et al. |
| 7,960,935 B2 | 6/2011 | Farritor et al. |
| 7,979,157 B2 | 7/2011 | Anvari |
| 3,021,358 A1 | 9/2011 | Doyle et al. |
| 8,179,073 B2 | 5/2012 | Farritor et al. |
| 8,231,610 B2 | 7/2012 | Jo et al. |
| 8,343,171 B2 | 1/2013 | Farritor et al. |
| 8,353,897 B2 | 1/2013 | Doyle et al. |
| 8,377,045 B2 | 2/2013 | Schena |
| 8,430,851 B2 | 4/2013 | Mcginley et al. |
| 8,604,742 B2 | 12/2013 | Farritor et al. |
| 8,636,686 B2 | 1/2014 | Minnelli et al. |
| 8,679,096 B2 | 3/2014 | Farritor et al. |
| 8,827,337 B2 | 9/2014 | Murata et al. |
| 8,828,024 B2 | 9/2014 | Farritor et al. |
| 8,834,488 B2 | 9/2014 | Farritor et al. |
| 8,864,652 B2 | 10/2014 | Diolaiti et al. |
| 8,888,687 B2 | 11/2014 | Ostrovsky et al. |
| 8,968,332 B2 | 3/2015 | Farritor et al. |
| 8,974,440 B2 | 3/2015 | Farritor et al. |
| 8,986,196 B2 | 3/2015 | Larkin et al. |
| 9,010,214 B2 | 4/2015 | Markvicka et al. |
| 9,060,781 B2 | 6/2015 | Farritor et al. |
| 9,089,256 B2 | 7/2015 | Tognaccini et al. |
| 9,089,353 B2 | 7/2015 | Farritor et al. |
| 9,138,129 B2 | 9/2015 | Diolaiti |
| 9,198,728 B2 * | 12/2015 | Wang .................. H04N 7/185 |
| 9,516,996 B2 | 12/2016 | Diolaiti et al. |
| 9,649,020 B2 | 5/2017 | Finlay |
| 9,717,563 B2 | 8/2017 | Tognaccini et al. |
| 9,743,987 B2 | 8/2017 | Farritor et al. |
| 9,757,187 B2 | 9/2017 | Farritor et al. |
| 9,770,305 B2 | 9/2017 | Farritor et al. |
| 9,789,608 B2 | 10/2017 | Itkowitz et al. |
| 9,814,640 B1 | 11/2017 | Khaligh |
| 9,816,641 B2 | 11/2017 | Bock-Aronson et al. |
| 9,849,586 B2 | 12/2017 | Rosheim |
| 9,857,786 B2 | 1/2018 | Cristiano |
| 9,888,966 B2 | 2/2018 | Farritor et al. |
| 9,956,043 B2 | 5/2018 | Farritor et al. |
| 10,008,017 B2 | 6/2018 | Itkowitz et al. |
| 10,111,711 B2 | 10/2018 | Farritor et al. |
| 10,137,575 B2 | 11/2018 | Itkowitz et al. |
| 10,159,533 B2 | 12/2018 | Moll et al. |
| 10,220,522 B2 | 3/2019 | Rockrohr |
| 10,258,425 B2 | 4/2019 | Mustufa et al. |
| 10,307,199 B2 | 6/2019 | Farritor et al. |
| 10,342,561 B2 | 7/2019 | Farritor et al. |
| 10,368,952 B2 | 8/2019 | Tognaccini et al. |
| 10,507,066 B2 | 12/2019 | DiMaio et al. |
| 10,555,775 B2 | 2/2020 | Hoffman et al. |
| 10,582,973 B2 | 3/2020 | Wilson et al. |
| 10,695,137 B2 | 6/2020 | Farritor et al. |
| 10,729,503 B2 | 8/2020 | Cameron |
| 10,737,394 B2 | 8/2020 | Itkowitz et al. |
| 10,751,136 B2 | 8/2020 | Farritor et al. |
| 10,751,883 B2 * | 8/2020 | Nahum .................. B25J 9/1664 |
| 10,806,538 B2 | 10/2020 | Farritor et al. |
| 10,966,700 B2 * | 4/2021 | Farritor ............ A61B 1/00154 |
| 11,032,125 B2 | 6/2021 | Farritor et al. |
| 11,298,195 B2 * | 4/2022 | Ye .......................... A61B 34/30 |
| 11,382,702 B2 | 7/2022 | Tognaccini et al. |
| 11,529,201 B2 | 12/2022 | Mondry et al. |
| 11,595,242 B2 | 2/2023 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0109780 A1 | 6/2003 | Coste-Maniere et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0225479 A1 | 12/2003 | Waled |
| 2003/0229268 A1 | 12/2003 | Uchiyama et al. |

(56) References Cited

U.S. PATENT DOCUMENTS

| | | |
|---|---|---|
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0070850 A1 | 3/2005 | Albrecht |
| 2005/0083460 A1 | 4/2005 | Hattori et al. |
| 2005/0095650 A1 | 5/2005 | Julius et al. |
| 2005/0096502 A1* | 5/2005 | Khalili ............... A61B 34/72 600/129 |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0177026 A1 | 8/2005 | Hoeg et al. |
| 2005/0234294 A1 | 10/2005 | Saadat et al. |
| 2005/0234435 A1 | 10/2005 | Layer |
| 2005/0272977 A1 | 12/2005 | Saadat et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0079889 A1 | 4/2006 | Scott |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0189845 A1 | 8/2006 | Maahs et al. |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258938 A1 | 11/2006 | Hoffman et al. |
| 2006/0258954 A1 | 11/2006 | Timberlake et al. |
| 2006/0261770 A1 | 11/2006 | Kishi et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0088277 A1 | 4/2007 | Mcginley et al. |
| 2007/0088340 A1 | 4/2007 | Brock et al. |
| 2007/0106113 A1 | 5/2007 | Ravo |
| 2007/0106317 A1 | 5/2007 | Shelton et al. |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1* | 7/2007 | Larkin ............... A61B 1/009 600/104 |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2007/0287884 A1 | 12/2007 | Schena |
| 2008/0004634 A1 | 1/2008 | Farritor et al. |
| 2008/0015565 A1 | 1/2008 | Davison |
| 2008/0015566 A1 | 1/2008 | Livneh |
| 2008/0021440 A1 | 1/2008 | Solomon |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0071289 A1* | 3/2008 | Cooper ............... A61B 1/0051 901/14 |
| 2008/0071290 A1 | 3/2008 | Larkin et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0168639 A1 | 7/2008 | Otake et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0002414 A1 | 1/2009 | Shibata et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1* | 2/2009 | Farritor ............... A61B 34/30 606/130 |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1* | 6/2009 | Yeung ............... B25J 9/047 606/130 |
| 2009/0171373 A1* | 7/2009 | Farritor ............... A61B 34/30 606/130 |
| 2009/0234369 A1* | 9/2009 | Bax ............... A61B 34/30 606/130 |
| 2009/0236400 A1* | 9/2009 | Cole ............... A61F 5/0083 227/180.1 |
| 2009/0240246 A1 | 9/2009 | Devill et al. |
| 2009/0247821 A1* | 10/2009 | Rogers ............... A61B 1/00098 600/104 |
| 2009/0248038 A1 | 10/2009 | Blumenkranz et al. |
| 2009/0281377 A1 | 11/2009 | Newell et al. |
| 2009/0299143 A1 | 12/2009 | Conlon et al. |
| 2009/0305210 A1 | 12/2009 | Guru et al. |
| 2009/0326322 A1 | 12/2009 | Diolaiti |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0026347 A1 | 2/2010 | Tizuka |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0101346 A1 | 4/2010 | Johnson et al. |
| 2010/0130986 A1 | 5/2010 | Mailloux et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |

(56) References Cited

U.S. PATENT DOCUMENTS

| | | |
|---|---|---|
| 2010/0250000 A1 | 9/2010 | Blumenkranz et al. |
| 2010/0262162 A1 | 10/2010 | Omori |
| 2010/0263470 A1 | 10/2010 | Bannasch et al. |
| 2010/0274079 A1 | 10/2010 | Kim et al. |
| 2010/0292691 A1 | 11/2010 | Brogna |
| 2010/0301095 A1 | 12/2010 | Shelton, IV et al. |
| 2010/0318059 A1 | 12/2010 | Farritor et al. |
| 2010/0331856 A1 | 12/2010 | Carlson et al. |
| 2011/0015569 A1 | 1/2011 | Kirschenman et al. |
| 2011/0020779 A1 | 1/2011 | Hannaford et al. |
| 2011/0071347 A1* | 3/2011 | Rogers ............... A61B 34/71 600/114 |
| 2011/0071544 A1 | 3/2011 | Steger et al. |
| 2011/0075693 A1 | 3/2011 | Kuramochi et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0107866 A1 | 5/2011 | Oka et al. |
| 2011/0152615 A1 | 6/2011 | Schostek et al. |
| 2011/0224605 A1 | 9/2011 | Farritor et al. |
| 2011/0230894 A1* | 9/2011 | Simaan ............... A61B 1/00183 606/130 |
| 2011/0237890 A1 | 9/2011 | Farritor et al. |
| 2011/0238079 A1 | 9/2011 | Hannaford et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |
| 2012/0016175 A1 | 1/2012 | Roberts et al. |
| 2012/0029727 A1 | 2/2012 | Sholev |
| 2012/0035582 A1 | 2/2012 | Nelson et al. |
| 2012/0059392 A1 | 3/2012 | Diolaiti |
| 2012/0078053 A1 | 3/2012 | Phee et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0221147 A1 | 8/2012 | Goldberg et al. |
| 2012/0253515 A1 | 10/2012 | Coste-Maniere et al. |
| 2013/0001970 A1 | 1/2013 | Suyama et al. |
| 2013/0041360 A1 | 2/2013 | Farritor et al. |
| 2013/0055560 A1 | 3/2013 | Nakasugi et al. |
| 2013/0125696 A1 | 5/2013 | Long |
| 2013/0131695 A1* | 5/2013 | Scarfogliero ........ A61B 34/30 606/130 |
| 2013/0178867 A1 | 7/2013 | Farritor et al. |
| 2013/0282023 A1 | 10/2013 | Burbank et al. |
| 2013/0304084 A1 | 11/2013 | Beira et al. |
| 2013/0325030 A1 | 12/2013 | Hourtash et al. |
| 2013/0325181 A1 | 12/2013 | Moore |
| 2013/0345717 A1 | 12/2013 | Markvicka et al. |
| 2013/0345718 A1 | 12/2013 | Crawford et al. |
| 2014/0039515 A1 | 2/2014 | Mondry et al. |
| 2014/0046340 A1 | 2/2014 | Wilson et al. |
| 2014/0055489 A1 | 2/2014 | Itkowitz et al. |
| 2014/0058205 A1 | 2/2014 | Frederick et al. |
| 2014/0100587 A1 | 4/2014 | Farritor et al. |
| 2014/0137687 A1 | 5/2014 | Nogami et al. |
| 2014/0221749 A1 | 8/2014 | Grant et al. |
| 2014/0232824 A1 | 8/2014 | DiMaio et al. |
| 2014/0276944 A1 | 9/2014 | Farritor et al. |
| 2014/0303434 A1 | 10/2014 | Farritor et al. |
| 2014/0371762 A1 | 12/2014 | Farritor et al. |
| 2015/0051446 A1* | 2/2015 | Farritor ............... A61B 1/0057 600/102 |
| 2015/0057537 A1 | 2/2015 | Dillon et al. |
| 2015/0157191 A1 | 6/2015 | Phee et al. |
| 2015/0223896 A1 | 8/2015 | Farritor et al. |
| 2015/0297299 A1 | 10/2015 | Yeung et al. |
| 2016/0066999 A1 | 3/2016 | Forgione et al. |
| 2016/0135898 A1 | 5/2016 | Frederick et al. |
| 2016/0291571 A1 | 10/2016 | Cristiano |
| 2016/0303745 A1 | 10/2016 | Rockrohr |
| 2017/0014197 A1 | 1/2017 | Mccrea et al. |
| 2017/0035526 A1 | 2/2017 | Farritor et al. |
| 2017/0078583 A1 | 3/2017 | Haggerty et al. |
| 2017/0252096 A1 | 9/2017 | Felder et al. |
| 2017/0354470 A1 | 12/2017 | Farritor et al. |
| 2018/0132956 A1 | 5/2018 | Cameron |
| 2018/0153578 A1 | 6/2018 | Cooper et al. |
| 2018/0338777 A1 | 11/2018 | Bonadio et al. |
| 2019/0059983 A1 | 2/2019 | Germain et al. |
| 2019/0090965 A1 | 3/2019 | Farritor et al. |
| 2019/0209262 A1 | 7/2019 | Mustufa et al. |
| 2019/0327394 A1 | 10/2019 | Ramirez et al. |
| 2020/0138534 A1 | 5/2020 | Garcia Kilroy et al. |
| 2020/0214775 A1 | 7/2020 | Farritor et al. |
| 2020/0330175 A1 | 10/2020 | Cameron |
| 2020/0368915 A1 | 11/2020 | Itkowitz et al. |

FOREIGN PATENT DOCUMENTS

| | | |
|---|---|---|
| CN | 102821918 | 12/2012 |
| CN | 104523309 A | 4/2015 |
| CN | 104582600 A | 4/2015 |
| CN | 104622528 A | 5/2015 |
| CN | 204337044 U | 5/2015 |
| CN | 105025826 A | 11/2015 |
| DE | 102010040405 | 3/2012 |
| EP | 0105656 A2 | 4/1984 |
| EP | 0279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 10/2015 |
| EP | 2937047 A1 | 10/2015 |
| JP | 5959371 A | 4/1984 |
| JP | 61165061 A | 7/1986 |
| JP | S6268293 A | 3/1987 |
| JP | 04144533 A | 5/1992 |
| JP | 05-115425 | 5/1993 |
| JP | 06507809 A | 9/1994 |
| JP | 06508049 A | 9/1994 |
| JP | 2006508049 | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004283940 A | 10/2004 |
| JP | 2004322310 | 11/2004 |
| JP | 2004329292 | 11/2004 |
| JP | 2006507809 | 3/2006 |
| JP | 2009106606 | 5/2009 |
| JP | 2009297809 A | 12/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| JP | 2012176489 A | 9/2012 |
| JP | 2012504017 A | 2/2015 |
| JP | 2015526171 A | 9/2015 |
| JP | 2016213937 A | 12/2016 |
| JP | 2017113837 A | 6/2017 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 1/2006 |
| WO | 2006079108 | 7/2006 |

(56) References Cited

FOREIGN PATENT DOCUMENTS

| | | |
|---|---|---|
| WO | 2007011654 | 1/2007 |
| WO | 2007111571 | 10/2007 |
| WO | 2007149559 | 12/2007 |
| WO | 2009014917 A2 | 1/2009 |
| WO | 2009023851 | 2/2009 |
| WO | 2009144729 | 12/2009 |
| WO | 2009158164 A1 | 12/2009 |
| WO | 2010039394 A1 | 4/2010 |
| WO | 2010042611 A1 | 4/2010 |
| WO | 2010046823 A1 | 4/2010 |
| WO | 2010050771 | 5/2010 |
| WO | 2010083480 A2 | 7/2010 |
| WO | 2011075693 | 6/2011 |
| WO | 2011118646 | 9/2011 |
| WO | 2011135503 | 11/2011 |
| WO | 2011163520 A2 | 12/2011 |
| WO | 2013009887 | 1/2013 |
| WO | 2013052137 A2 | 4/2013 |
| WO | 2013106569 A2 | 7/2013 |
| WO | 2014011238 | 1/2014 |
| WO | 2014025399 A1 | 2/2014 |
| WO | 2014144220 A1 | 9/2014 |
| WO | 2014146090 A1 | 9/2014 |
| WO | 2015009949 A2 | 1/2015 |
| WO | 2015031777 A1 | 3/2015 |
| WO | 2015088655 A1 | 6/2015 |
| WO | 2016077478 A1 | 5/2016 |
| WO | 2017024081 A1 | 2/2017 |
| WO | 2017064303 A1 | 4/2017 |
| WO | 2017201310 A1 | 11/2017 |
| WO | 2018045036 A1 | 3/2018 |

OTHER PUBLICATIONS

Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., "Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.

Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rooties: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-13.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimenal Results," Annals of Biomedical Engineering 31:1372-1382.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Southern Surgeons Club (1991), "A prospective analysis of 1518 laparoscopic cholecystectomies," N. Eng. 1 Med. 324 (16): 1073-1078.
Suzumori et al., "Development of Flexible Microactuator and its Applications to Robotics Mechanisms," Proceedings of the IEEE International Conference on Robotics and Automation, 1991: 1622-1627.

(56) References Cited

OTHER PUBLICATIONS

Wolfe et al. (1991), Endoscopic Cholecystectomy: An analysis of Complications, Arch. Surg. 1991; 126: 1192-1196.

Mack et al., "Present Role of Thoracoscopy in the Diagnosis and Treatment of Diseases of the Chest," Ann Thorac Surgery, 1992; 54: 403-409.

Peters, "Minimally Invasive Colectomy: Are the Potential Benefits Realized?" Dis Colon Rectum 1993; 36: 751-756.

Tendick et al. (1993), "Sensing and Manipulation Problems in Endoscopic Surgery: Experiment, Analysis, and Observation," Presence 2(1): 66-81.

Sackier et al., "Robotically assisted laparoscopic surgery," Surgical Endoscopy, 1994; 8:63-6.

Stiff et al., "Long-term Pain: Less Common After Laparoscopic than Open Cholecystectomy," British Journal of Surgery, 1994; 81: 1368-1370.

Slatkin et al., "The Development of a Robotic Endoscope," Proceedings of the 1995 IEEE International Conference on Robotics and Automation, pp. 162-171, 1995.

Taylor et al., "A Telerobotic Assistant for Laparoscopic Surgery," IEEE Eng Med Biol, 1995; 279-87.

Way et al., EDITORS, "Fundamentals of Laparoscopic Surgery," Churchill Livingstone Inc., 1995; 14 pp.

Guo et al., "Micro Active Guide Wire Catheter System—Characteristic Evaluation, Electrical Model* and Operability Evaluation of Micro Active Catheter," Proceedings of the 1996 IEEE International Conference on Robotics and Automation, Apr. 1996; 2226-2231.

Schippers et al. (1996), "Requirements and Possibilities of Computer-Assisted Endoscopic Surgery," In: Computer Integrated Surgery: Technology and Clinical Applications, pp. 561-565.

Liem et al., "Comparison of Conventional Anterior Surgery and Laparoscopic Surgery for Inguinal-hernia Repair," New England Journal of Medicine, 1997; 336 (22):1541-1547.

Kazemier et al. (1998), "Vascular Injuries During Laparoscopy," J. Am. Coli. Surg. 186(5): 604-5.

Palm. William. "Rapid Prototyping Primer" May 1998 (revised Jul. 30, 2002) (http://www.me.psu.edu/lamancusa/ rapidpro/primer/chapter2.htm), 12 pages.

Tendick et al., "Applications of Micromechatronics in Minimally Invasive Surgery," IEEE/ASME Transactions on Mechatronics, 1998; 3(1): 34-42.

Worn et al., "Espirit Project No. 33915: Miniaturised Robot for Micro Manipulation (MINIMAN)," Nov. 1998, http://www.ipr.ira.ujka.de/-microbot/miniman.

Macfarlane et al., "Force-Feedback Grasper Helps Restore the Sense of Touch in Minimally Invasive Surgery," Journal of Gastrointestinal Surgery, 1999; 3: 278-285.

Rosen et al., "Force Controlled and Teleoperated Endoscopic, Grasper for Minimally Invasive Surgery- Experimental Performance Evaluation," IEEE Transactions of Biomedical Engineering, Oct. 1999; 46(10): 1212-1221.

Gong et al., "Wireless endoscopy," Gastrointestinal Endoscopy 2000; 51 (6): 725-729.

Heikkinen et al., "Comparison of laparoscopic and open Nissen fundoplication two years after operation: A prospective randomized trial," Surgical Endoscopy, 2000; 14:1019-1023.

Li et al. (2000), "Microvascular Anastomoses Performed in Rats Using a Microsurgical Telemanipulator," Comp. Aid. Surg., 5: 326-332.

Ishiyama et al., "Spiral-type Micro-machine for Medical Applications," 2000 International Symposium on Micromechatronics and Human Science, 2000; 65-69.

Meron, "The development of the swallowable video capsule (M2A)," Gastrointestinal Endoscopy 2000; 52 6: 817-819.

Salky, "What is the Penetration of Endoscopic Techniques into Surgical Practice?" Digestive Surgery 2000; 17:422-426.

Schurr et al., "Robotics and Telemanipulation Technologies for Endoscopic Surgery," Surgical Endoscopy, 2000; 14:375-381.

Abbou et al., "Laparoscopic Radical Prostatectomy with a Remote Controlled Robot," The Journal of Urology, Jun. 2001; 165: 1964-1966.

Horgan et al., "Technical Report: Robots in Laparoscopic Surgery," Journal of Laparoendoscopic & Advanced Surgical Techniques, 2001; 11(6): 415-419.

Kang et al., "Robotic Assistants Aid Surgeons During Minimally Invasive Procedures," IEEE Engineering in Medicine and Biology, Jan .- Feb. 2001: 94-104.

Lafullarde et al., "Laparoscopic Nissen Fundoplication: Five-year Results and Beyond," Arch/Surg, Feb. 2001; 136: 180-184.

Mack, "Minimally Invasive and Robotic Surgery," JAMA, Feb. 2001; 285(5): 568-572.

Peirs et al., "A miniature manipulator for integration in a self-propelling endoscope," Sensors and Actuators A, 2001, 92: 343-349.

Yu et al., "Microrobotic Cell Injection," Proceedings of the 2001 IEEE International Conference on Robotics and Automation, May 2001: 620-625.

Yu, Bsn, Rn, "M2ATM Capsule Endoscopy A Breakthrough Diagnostic Tool for Small Intestine Imagining, " vol. 25, No. 1, 2001, Gastroenterology Nursing, pp. 24-27.

Guo et al., "Fish-like Underwater Microrobot with 3 DOF," Proceedings of the 2002 IEEE International Conference on Robotics & Automation, May 2002; 738-743.

Leggett et al. (2002), "Aortic injury during laparoscopic Fundoplication," Surg. Endoscopy 16(2): 362.

Mei et al., "Wireless Drive and Control of a Swimming Microrobot," Proceedings of the 2002 IEEE International Conference on Robotics & Automation, May 2002: 1131-1136.

Melvin et al., "Computer-Enhanced vs. Standard Laparoscopic Antireflux Surgery," J Gastrointest Surg 2002; 6: 11-16.

Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

Munro (2002), "Laparoscopic access: complications, technologies, and techniques," Curro Opin. Obstet. Gynecol., 14(4): 365-74.

Nio et al., "Efficiency of manual vs robotical (Zeus) assisted laparoscopic surgery in the performance of standardized tasks," Surg Endosc, 2002; 16: 412-415.

Phee et al., "Analysis and Development of Locomotion Devices for the Gastrointestinal Tract," IEEE Transactions on Biomedical Engineering, vol. 49, No. 6, Jun. 2002: 613-616.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON - A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Robot-Assisted surgical systems: a new era in laparoscopic surgery," Ann R. Coll Surg Engl. 2002; 84: 223-226.

Rosen et al., Objective Evaluation of Laparoscopic Skills Based on Haptic Information and Tool/Tissue Interactions, Computer Aided Surgery, vol. 7, Issue 1, pp. 49-61, Jul. 2002.

Satava, "Surgical Robotics: The Early Chronicles," Surgical Laparoscopy, Endoscopy & Percutaneous Techniques, 2002; 12(1):6-16.

Thomann et al., "The Design of a new type of Micro Robot for the Intestinal Inspection," Proceedings of the 2002 IEEE Intl. Conference on Intelligent Robots and Systems, Oct. 2002: 1385-1390.

Orlando et al. (2003), "Needle and Trocar Injuries in Diagnostic Laparoscopy under Local Anesthesia: What Is the True Incidence of These Complications?" Journal of Laparoendoscopic & Advanced Surgical Techniques, 13(3): 181-184.

Lehman et al., Dexterous miniature in vivo robot for NOTES, 2009, IEEE, p. 244-249.

Mihelj et al., ARMin II—7 DoF rehabilitation robot: mechanics and kinematics, 2007, IEEE, p. 4120-4125.

Zhang et al., Cooperative robotic assistant for laparoscopic surgery: CoBRASurge, 2009, IEEE, p. 5540-5545.

(56) References Cited

OTHER PUBLICATIONS

Riviere et al., "Toward Active Tremor Canceling in Handheld Microsurgical Instruments," IEEE Transactions on Robotics and Automation, Oct. 2003, 19(5): 793-800.
Albers et al., Design and development process of a humanoid robot upper body through experimentation, 2004, IEEE, p. 77-92 (Year: 2004).
Glukhovsky et al., "The development and application of wireless capsule endoscopy," Int. J. Med. Robot. Comput. Assist. Surgery, 2004; 1(1): 114-123.
Hanly et al., "Robotic Abdominal Surgery," The American Journal of Surgery, 2004; 188 (Suppl. to Oct. 1994); 19S-26S.
Hanly et al., "Value of the SAGES Learning Center in introducing new technology," Surgical Endoscopy, 2004; 19 (4): 477-483.
Hissink, "Olympus Medical develops capsule camera technology," Dec. 2004, accessed Aug. 29, 2007, http://www.letsgodigital.org, 3 pp.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Menciassi et al., "Locomotion of a Leffed Capsule in the Gastro-intestinal Tract: Theoretical Study and Preliminary Technological Results," IEEE Int. Conf. on Engineering in Medicine and Biology, San Francisco, CA, pp. 2767-2770, Sep. 2004.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 p. , 2004.
Oleynikov et al., "In Vivo Camera Robots Provide Improved Vision for Laparoscopic Surgery," Computer Assisted Radiology and Surgery (CARS), Chicago, IL, Jun. 23 - 26, 2004b.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, pp. 239-240, 2004.
Rentschler et al., "In Vivo Robots for Laparoscopic Surgery," Studies in Health Technology and Infonnatics - Medicine Meets Virtual Reality, ISO Press, Newport Beach, CA, 2004a, 98: 316-322.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28 - Oct. 2, 2004; pp. 1-9.
Jagannath et al., "Peroral transgastric endoscopic ligation of fallopian tubes with long-term survival in a porcine model," Gastrointestinal Endoscopy, 2005; 61 (3): 449-453.
Kantsevoy et al., "Endoscopic gastrojejunostomy with survival in a porcine model," Gastrointestinal Endoscopy, 2005; 62(2): 287-292.
Menciassi et al., "Shape memory alloy clamping devices of a capsule for monitoring tasks in the gastrointestinal tract," J. Micromech. Microeng, 2005; 15: 2045-2055.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
Park et al., "Experimental studies of transgastric gallbladder surgery: cholecystectomy and cholecystogastric anastomosis (videos)," Gastrointestinal Endoscopy, 2005; 61 (4): 601-606.
Patronik et al., "Preliminary evaluation of a mobile robotic device for navigation and intervention on the beating heart," Computer Aided Surgery, 10(4): 225-232, Jul. 2005.
Platt et al., "In Vivo Robotic Cameras can Enhance Imaging Capability During Laparoscopic Surgery," from the Proceedings of the Society of American Gastrointestinal Endoscopic Surgeons (SAGES) Scientific Conference, Ft. Lauderdale, FL, Apr. 13-16, 2005; 1 pg.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, April 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Toward In Vivo Mobility," Studies in Health Technology and Infonnatics - Medicine Meets Virtual Reality, ISO Press, Long Beach, CA, 2005a, III: 397-403.
Rosen et al., "Spherical Mechanism Analysis of a Surgical Robot for Minimally Invasive Surgery - Analytical and Experimental Approaches," Studies in Health Technology and Infonnatics-Medicine Meets Virtual Reality, pp. 442-448, Jan. 2005.
Smart Pill "Fastastic Voyage: Smart Pill to Expand Testing," http://www.smartpilldiagnostics.com, Apr. 13, 2005, 1 pg.
Strong et al., "Efficacy of Novel Robotic Camera vs. a Standard Laproscopic Camera," Surgical Innovation vol. 12, No. 4, Dec. 2005, Westminster Publications, Inc., pp. 315-318.
Kantsevoy et al., "Transgastric endoscopic splenectomy," Surgical Endoscopy, 2006; 20: 522-525.
Ko et al., "Per-Oral transgastric abdominal surgery," Chinese Journal of Digestive Diseases, 2006; 7: 67-70.
Micron, http://www.micron.com, 2006, 1/4-inch VGA NTSC/PAL CMOS Digital Image Sensor, 98 pp.
Rentschler et al., "Mechanical Design of Robotic In Vivo Wheeled Mobility," ASME Journal of Mechanical Design, 2006a; pp. 1-11, Accepted.
Rentschler et al., "Miniature in vivo robots for remote and harsh environments," IEEE Transaction on Information Technology in Biomedicine, Jan. 2006; 12(1): pp. 66-75.
Rentschler et al., "Mobile In Vivo Biopsy Robot," IEEE International Conference on Robotics and Automation, Orlando, Florida, May 2006; 4155-4160.
Rentschler et al., "Mobile In Vivo Biopsy and Camera Robot," Studies in Health and Infonnatics Medicine Meets Virtual Reality, vol. 119: 449-454, IOS Press, Long Beach, CA, 2006e.
Rentschler et al., "Mobile In Vivo Camera Robots Provide Sole Visual Feedback for Abdominal Exploration and Cholecystectomy," Journal of Surgical Endoscopy, 20-1: 135-138, 2006b.
Rentschler et al., "Natural Orifice Surgery with an Endoluminal Mobile Robot," The Society of American Gastrointestinal Endoscopic Surgeons, Dallas, TX, April 2006d.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Sharp LL-151-3D, http://www.sharp3d.com, 2006, 2 pp.
Crystal Eyes, http://www.reald.com, 2007 (Stereo 3D visualization for CAVEs, theaters and immersive environments), 1 pg.
O'Neill, "Surgeon takes new route to gallbladder," The Oregonian, Jun. 2007; 2 pp.
Park et al., "Trocar-less Instrumentation for Laparoscopy: Magnetic Positioning of Intra-abdominal Camera and Retractor," Ann Surg, Mar. 2007; 245(3): 379-384.
Rentschler et al., "An In Vivo Mobile Robot for Surgical Vision and Task Assistance," Journal of Medical Devices, Mar. 2007; vol. 1: 23-29.
Rentschler et al., "In vivo Robotics during the NEEMO 9 Mission," Medicine Meets Virtual Reality, Feb. 2007; 1 pg.
Schwartz, "In the Lab: Robots that Slink and Squirm," The New York Times, Mar. 27, 2007, 4 pp.
Gopura et al., Mechanical designs of active upper-limb exoskeleton robots: State-of-the-art and design difficulties, 2009, IEEE, p. 178-187 (Year: 2009).
Xu et al., "System Design of an Insertable Robotic Effector Platform for Single Access (SPA) Surgery" , The 2009 IEEE/RSJ International Conference on Intelligent Robots and Systems, Oct. 11-15, 2009, St. Louis Mo USA pp. 5546-5552.
Gopura et al., A brief review on upper extremity robotic exoskeleton systems, 2011, IEEE, p. 346-351 (Year: 2011).
Midday Jeff et al., "Material Handling System for Robotic natural Orifice Surgery,", Proceedings of the 2011 Design of medical Devices Conference, Apr. 12-14, 2011, Minneapolis, MN 4 pages.

(56) References Cited

OTHER PUBLICATIONS

Keller et al., Design of the pediatric arm rehabilitation robot ChARMin, 2014, IEEE, p. 530-535 (Year: 2014).

* cited by examiner

ROBOTIC SURGICAL DEVICES WITH TRACKING CAMERA TECHNOLOGY AND RELATED SYSTEMS AND METHODS

CROSS-REFERENCE TO RELATED APPLICATION(S)

This application claims priority as a continuation of U.S. application Ser. No. 16/144,807, filed Sep. 27, 2018 and entitled "Robotic Surgical Devices with Tracking Camera Technology and Related Systems and Methods," which Issued as U.S. Pat. No. 11,051,894 on Jul. 6, 2021, which claims the benefit under 35 U.S.C. § 119(e) to U.S. Provisional Application 62/564,076, filed Sep. 27, 2017 and entitled "Robotic Surgical Devices with Camera Tracking and Related Systems and Methods," which is hereby incorporated herein by reference in its entirety.

FIELD OF THE INVENTION

The implementations disclosed herein relate to various medical devices and related components, including robotic and/or in vivo medical devices and related components. Certain implementations include various robotic medical devices, including robotic devices that are disposed within a body cavity and positioned using a support component disposed through an orifice or opening in the body cavity and further including a camera that is positioned through the support component and can be operated to manually or automatically track the arms or end effectors of the robotic device. Further implementations relate to methods and devices for operating the above devices.

BACKGROUND OF THE INVENTION

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various robotic surgical systems, including certain systems having camera lumens constructed and arranged to receive various camera systems, including tracking camera systems. Further implementations relate to surgical insertion devices constructed and arranged to be used to insert various surgical devices into a cavity of a patient while maintaining insufflation of the cavity.

In various Examples, a system of one or more computers can be configured to perform particular operations or actions through software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In Example 1, a robotic surgical system, comprising a device body constructed and arranged to be positioned at least partially within a body cavity of a patient through an incision, the device body comprising: a first robotic surgical arm operably coupled to the device body and comprising a first end effector; a second robotic surgical arm operably coupled to the device body and comprising a first end effector; a camera lumen defined in the device body; a positionable camera constructed and arranged to provide views of the first and second end effectors; and a surgical console comprising a processor constructed and arranged to execute an algorithm to position the positionable camera.

In Example 2, of Example of claim 1, wherein the positionable camera comprises a tip constructed and arranged to be capable of both pitch and yaw.

In Example 3, of Example of claim 1, wherein the processor is constructed and arranged to execute a control algorithm for positioning of the first and second robotic surgical arms.

In Example 4, of Example of claim 3, wherein the control algorithm is constructed and arranged to establish a camera reference frame and a robot reference frame.

In Example 5, of Example of claim 4, wherein the processor is configured to align the camera reference frame with the robot reference frame and re-position the positionable camera.

In Example 6, of Example of claim 4, wherein the robot coordinate frame is established relative to the device body and is defined by orthogonal unit vectors xR, yR, and zR.

In Example 7, of Example of claim 4, wherein the camera coordinate frame is defined by orthogonal unit vectors xC, yC, and zC.

In Example 8, of Example of claim 4, wherein the processor is configured to define locations PL and PR for the first and second end effectors, respectively.

In Example 9, of Example of claim 8, wherein the processor is configured to establish Midpoint PLPR between the end effectors via PL and PR.

In Example 10, of Example of claim 9, wherein the camera reference frame has an origin and the processor is configured to align the Midpoint PLPR and reposition the positionable camera.

In Example 11, a robotic surgical system, comprising a robotic surgical device comprising a first robotic surgical arm operably coupled to the device body and comprising a first end effector; a second robotic surgical arm operably coupled to the device body and comprising a first end effector; and a camera lumen defined in the device body; a positionable camera comprising an articulating tip and constructed and arranged to be inserted into the robotic surgical device such that the tip is oriented to view the first and second end effectors; and a surgical console comprising a processor constructed and arranged to execute a control algorithm to position the positionable camera, wherein the control algorithm is constructed and arranged to establish a camera reference frame, establish a robot reference frame, and position the camera tip relative to the camera reference frame or robot reference frame.

In Example 12, of Example of claim 11, wherein the robot coordinate frame is established relative to the device body and is defined by orthogonal unit vectors xR, yR, and zR.

In Example 13, of Example of claim 11, wherein the camera coordinate frame is defined by orthogonal unit vectors xC, yC, and zC.

In Example 14, of Example of claim 11, wherein the processor is configured to define locations PL and PR for the first and second end effectors, respectively.

In Example 15, of Example of claim 14, wherein the processor is configured to establish Midpoint PLPR between the end effectors via PL and PR, and wherein the camera reference frame has an origin and the processor is configured to align the Midpoint PLPR and reposition the positionable camera.

In Example 16, a robotic surgical system, comprising: a robotic surgical device comprising: a first robotic surgical arm operably coupled to the device body and comprising a first end effector; and a second robotic surgical arm operably coupled to the device body and comprising a first end effector; a positionable camera comprising an articulating tip and constructed and arranged to be inserted into the robotic surgical device such that the tip is oriented to view the first and second end effectors; and a processor constructed and arranged to execute a control algorithm to position the positionable camera, wherein the control algorithm is constructed and arranged to: establish a camera reference frame defined by orthogonal unit vectors xC, yC, and zC, establish a robot reference frame established relative to the device body and is defined by orthogonal unit vectors xR, yR, and zR, and position the camera tip relative to the camera reference frame or robot reference frame.

In Example 17, of Example of claim 16, further comprising a robot clamp constructed and arranged to rotatably couple the robotic surgical device to a support arm.

In Example 18, of Example of claim 16, wherein the robot clamp further comprises a release button and a clothespin member.

In Example 19, of Example of claim 16, further comprising an interface pod.

In Example 20, of Example of claim 16, further comprising an indicator light.

Other embodiments of these Examples include corresponding computer systems, apparatus, and computer programs recorded on one or more computer storage devices, each configured to perform the actions of the methods.

While multiple implementations are disclosed, still other implementations of the present invention will become apparent to those skilled in the art from the following detailed description, which shows and describes illustrative implementations of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1A:
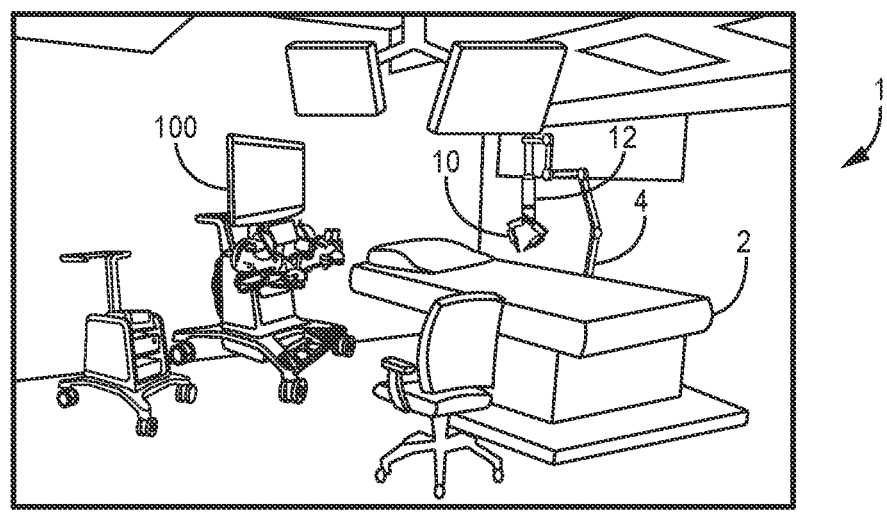
FIG. 1A is a side view schematic view of the robotic surgical system, according to one embodiment.

The various systems and devices disclosed herein relate to devices for use in medical procedures and systems. More specifically, various implementations relate to various medical devices, including robotic devices having tracking camera systems and related methods and systems, including, in some implementations, controlling consoles and other devices to provide complete systems.

It is understood that the various implementations of robotic devices and related methods and systems disclosed herein can be incorporated into or used with any other known medical devices, systems, and methods. For example, the various implementations disclosed herein may be incorporated into or used with any of the medical devices and systems disclosed in U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), U.S. Pat. No. 8,179,073 (issued May 15, 2011, and entitled "Robotic Devices with Agent Delivery Components and Related Methods"), U.S. Pat. No. 8,343,171 (issued Jan. 1, 2013 and entitled "Methods and Systems of Actuation in Robotic Devices"), U.S. Pat. No. 8,679,096 (issued Mar. 25, 2014 and entitled "Multifunctional Operational Component for Robotic Devices"), U.S. Pat. No. 8,834,488 (issued Sep. 16, 2014 and entitled "Magnetically Coupleable Surgical Robotic Devices and Related Methods"), U.S. Pat. No. 8,894,633 (issued Nov. 25, 2014 and entitled "Modular and Cooperative Medical Devices and Related Systems and Methods"), U.S. Pat. No. 8,968,267 (issued Mar. 3, 2015 and entitled "Methods and Systems for Handling or Delivering Materials for Natural Orifice Surgery"), U.S. Pat. No. 8,968,332 (issued Mar. 3, 2015 and entitled "Magnetically Coupleable Robotic Devices and Related Methods"), U.S. Pat. No. 8,974,440 (issued Mar. 10, 2015 and entitled "Modular and Cooperative Medical Devices and Related Systems and Methods"), U.S. Pat. No. 9,010,214 (Apr. 21, 2015 and entitled "Local Control Robotic Surgical Devices and Related Methods"), U.S. Pat. No. 9,060,781 (issued Jun. 23, 2015 and entitled "Methods, Systems, and Devices Relating to Surgical End Effectors"), U.S. Pat. No. 9,089,353 (issued Jul. 28, 2015 and entitled "Robotic Surgical Devices, Systems, and Related Methods"), U.S. Pat. No. 9,498,292 (issued Nov. 22, 2016 and entitled "Single Site Robotic Devices and Related Systems and Methods"), U.S. Pat. No. 9,579,088 (issued Feb. 28, 2017 and entitled "Methods, Systems, and Devices for Surgical Visualization and Device Manipulation"), U.S. Pat. No. 9,743,987 (Aug. 29, 2017 and entitled "Methods, Systems, and Devices Relating to Robotic Surgical Devices, End Effectors, and Controllers"), U.S. Pat. No. 9,770,305 (issued Sep. 26, 2017 and entitled "Robotic Surgical Devices, Systems, and Related Methods"), and U.S. Pat. No. 9,888,966 (issued Feb. 13, 2018 and entitled "Methods, Systems, and Devices Relating to Force Control Surgical Systems), all of which are hereby incorporated herein by reference in their entireties.

Further, the various implementations disclosed herein may be incorporated into or used with any of the medical devices and systems disclosed in copending U.S. Published Applications 2014/0046340 (filed Mar. 15, 2013 and entitled "Robotic Surgical Devices, Systems, and Related Methods"), 2014/0058205 (filed Jan. 10, 2013 and entitled "Methods, Systems, and Devices for Surgical Access and Insertion"), 2014/0303434 (filed Mar. 14, 2014 and entitled "Robotic Surgical Devices, Systems, and Related Methods"), 2015/0051446 (filed Jul. 17, 2014 and entitled "Robotic Surgical Devices, Systems, and Related Methods"), 2016/0074120 (filed Sep. 14, 2015, and entitled "Quick-Release End Effectors and Related Systems and Methods"), 2016/0135898 (filed Nov. 11, 2015 entitled "Robotic Device with Compact Joint Design and Related Systems and Methods"), 2016/0157709 (filed Feb. 8, 2016 and entitled "Medical Inflation, Attachment, and Delivery Devices and Related Methods"), 2017/0035526 (filed Aug. 3, 2016 and entitled "Robotic Surgical Devices, Systems, and Related Methods"), 2017/0354470 (filed May 18, 2017 and entitled "Robotic Surgical Devices, Systems, and Related Methods"), 2018/0055584 (filed Aug. 30, 2017 and entitled "Robotic Device with Compact Joint Design and an Additional Degree of Freedom and Related Systems and Methods"), 2018/0056527 (filed Aug. 25, 2017 and entitled "Quick-Release End Effector Tool Interface"), 2018/0140377 (filed Nov. 22, 2017 and entitled "Gross Positioning Device and Related Systems and Methods"), 2018/0147019 (filed Nov. 29, 2017 and entitled "User Controller with User Presence Detection and Related Systems and Methods"), and 2018/0161122 (filed Dec. 14, 2017 and entitled "Releasable Attachment Device for Coupling to Medical Devices and Related Systems and Methods"), all of which are hereby incorporated herein by reference in their entireties. In addition, the various implementations disclosed herein may be incorporated into or used with any of the medical devices and systems disclosed in U.S. Application 62/614,127 (filed Jan. 5, 2018), which is hereby incorporated herein by reference in its entirety.

Certain device and system implementations disclosed in the patents and/or applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations provide for insertion of the present invention into the cavity while maintaining sufficient insufflation of the cavity. Further implementations minimize the physical contact of the surgeon or surgical users with the present invention during the insertion process. Other implementations enhance the safety of the insertion process for the patient and the present invention. For example, some implementations provide visualization of the present invention as it is being inserted into the patient's cavity to ensure that no damaging contact occurs between the system/device and the patient. In addition, certain implementations allow for minimization of the incision size/length. Further implementations reduce the complexity of the access/insertion procedure and/or the steps required for the procedure. Other implementations relate to devices that have minimal profiles, minimal size, or are generally minimal in function and appearance to enhance ease of handling and use.

As in manual laparoscopic procedures, a known insufflation system can be used to pump sterile carbon dioxide (or other gas) into the patient's abdominal cavity. This lifts the abdominal wall from the organs and creates space for the robot. In certain implementations, the system has no direct interface with the insufflation system. Alternatively, the system can have a direct interface to the insufflation system.

In certain implementations, the insertion port is a known, commercially-available flexible membrane placed transabdominally to seal and protect the abdominal incision. This off-the-shelf component is the same device used in the same way for Hand-Assisted Laparoscopic Surgery (HALS). The only difference is that the working arms of the robot are inserted into the abdominal cavity through the insertion port rather than the surgeon's hand. The robot body seals against the insertion port, thereby maintaining insufflation pressure. The port is single-use and disposable. Alternatively, any known port can be used.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations, and the related systems. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one implementation these triangular or quadrangular devices can be positioned inside the body cavity of a patient in the same fashion as those devices discussed and disclosed above.

The various system implementations described herein are used to perform robotic surgery. Further, the various implementations disclosed herein can be used in a minimally invasive approach to a variety of procedures that are typically performed "open" by known technologies, with the potential to improve clinical outcomes and health care costs, including, for example, general surgery applications in the abdominal cavity, such as, for example, colon resection and other known procedures. Further, the various implementations disclosed herein can be used in place of the known mainframe-like laparoscopic surgical robots that reach into the body from outside the patient. That is, the less-invasive robotic systems, methods, and devices according to the implementations disclosed herein feature small, self-contained surgical devices that are inserted in their entireties through a single incision in the patient's abdomen. Designed to utilize existing tools and techniques familiar to surgeons, the devices disclosed herein will not require a dedicated operating room or specialized infrastructure, and, because of their much smaller size, are expected to be significantly less expensive than existing robotic alternatives for laparoscopic surgery. Due to these technological advances, the various implementations herein could enable a minimally invasive approach to procedures performed in open surgery today. In certain implementations, the various systems described herein are based on and/or utilize techniques used in manual laparoscopic surgery including insufflation of the abdominal cavity and the use of ports to insert tools into the abdominal cavity.

As will be described in additional detail below, components of the various system implementations disclosed or contemplated herein include a control console and a robot having a tracking camera system. The robot implementations are constructed and arranged to be inserted into the insufflated abdominal cavity. The tracking camera system can be an integrated camera system that captures a view of the surgical target and can be manually or automatically controlled to track and capture an ongoing view of the arms and/or end effectors of the robotic device. The surgeon can then use that view on a display to help control the robot's movements. In certain implementations, the camera is designed so that it can be removed so it can be cleaned and used in other applications.

In other implementations as will be discussed in further detail herein, the system can include disposable or permanent sleeves positioned on or attached to the robotic device, an electro-surgery cautery generator, an insertion port, a support arm/structure, a camera, remote surgical displays, end-effectors (tools), an interface pod, a light source, and other system components.

The various implementations are disclosed in additional detail in the attached figures, which may include some written description therein.

Figure 1B:
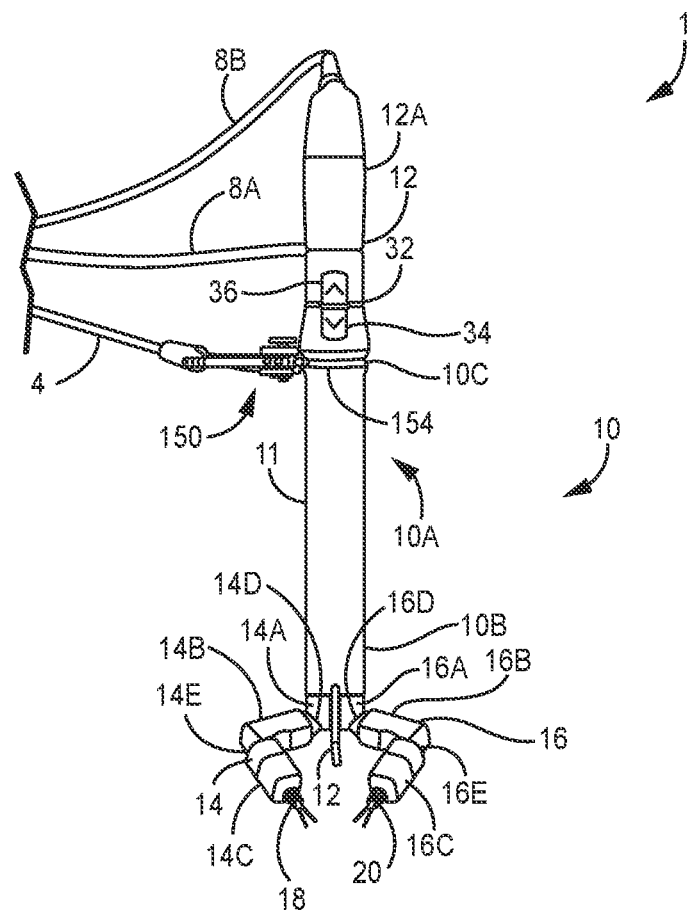
FIG. 1B is a front view of the robotic surgical system showing the robotic device with an engaged positionable camera, according to one embodiment.

According to one implementation, the Robotically Assisted Surgical Device (RASD) system 1 has several components. In one such implementation, and as shown in FIG. 1A and FIG. 1B, a surgical robotic device 10 having a robotically articulated camera 12 disposed therein and an external surgeon control console 100 is provided. In the implementation of FIG. 1A, the robotic device 10 and the camera 12 are shown mounted to the operating table 2 using a robot support arm 4, in accordance with one implementation. The system 1 can be, in certain implementations, operated by the surgeon and one surgical assistant.

Figure 2A:
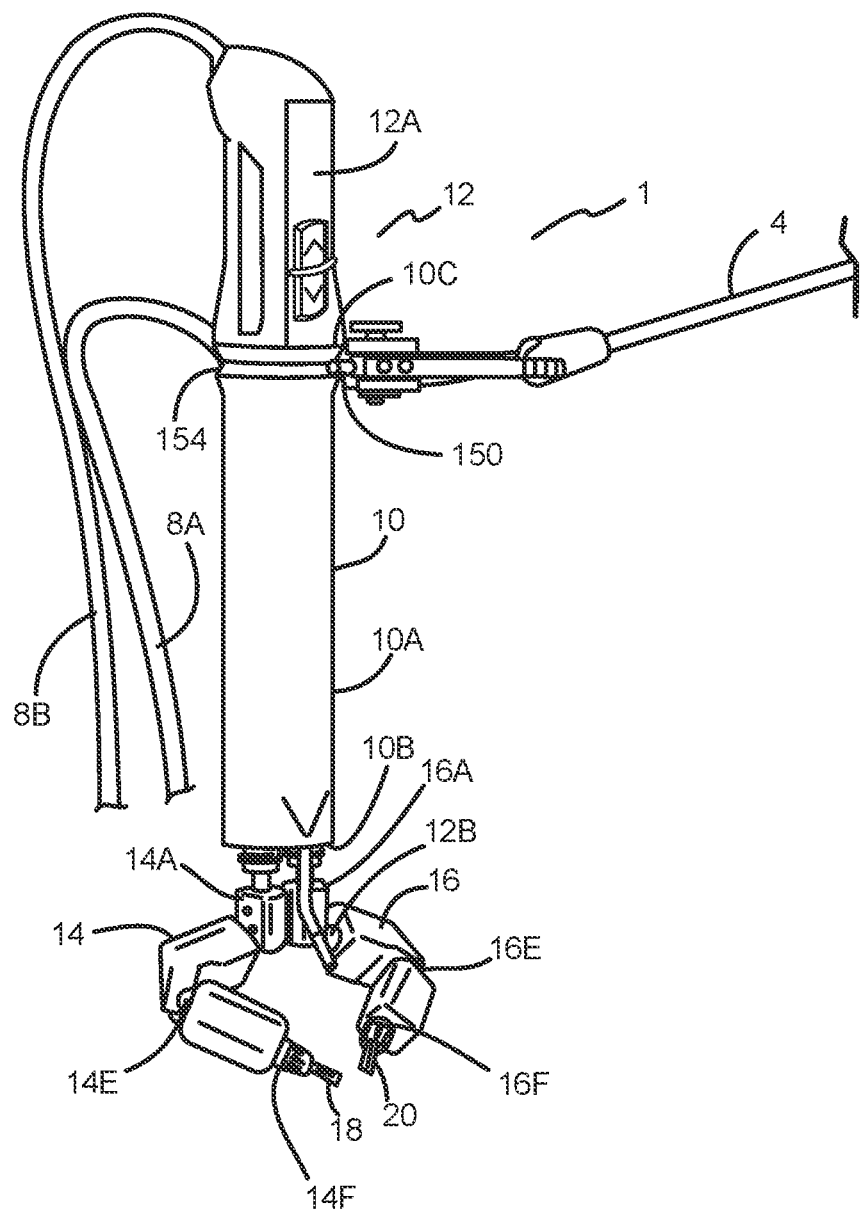
FIG. 2A is three-quarters front view of the robotic device with an engaged positionable camera, according to one embodiment.

FIG. 1B and FIG. 2A depict exemplary implementations of the robotic device 10 having a body 10A (or torso) having a distal end 10B and proximal end 10C, with the camera 12 disposed therein, as has been previously described. Briefly, the robotic device 10 has two robotic arms 14, 16 operably coupled thereto and a camera component or "camera" 12 disposed between the two arms 14, 16 and positionable therein. That is, device 10 has a first (or "right") arm 14 and a second (or "left") arm 16, both of which are operably coupled to the device 10 as discussed in additional detail below. The device 10 as shown has a casing (also referred to as a "cover" or "enclosure") 11. The device 10 is also referred to as a "device body" 10A and has two rotatable cylindrical components (also referred to as "shoulders" or "turrets"): a first (or "right") shoulder 14A and a second (or "left") shoulder 16A. Each arm 14, 16 also has an upper arm (also referred to herein as an "inner arm," "inner arm assembly," "inner link," "inner link assembly," "upper arm assembly," "first link," or "first link assembly") 14B, 16B, and a forearm (also referred to herein as an "outer arm," "outer arm assembly," "outer link," "outer link assembly,"

"forearm assembly," "second link," or "second link assembly") 14C, 16C. The right upper arm 14B is operably coupled to the right shoulder 14A of the body 10A at the right shoulder joint 14D and the left upper arm 16B is operably coupled to the left shoulder 16A of the body 10 at the left shoulder joint 16D. Further, for each arm 14, 16, the forearm 14C, 16C is rotatably coupled to the upper arm 14B, 16B at the elbow joint 14E, 16E.

In various implementations, the device 10 and each of the links of the arms 14, 16 contain a variety of actuators or motors. In one embodiment, any of the motors discussed and depicted herein can be brush or brushless motors. Further, the motors can be, for example, 6 mm, 8 mm, or 10 mm diameter motors. Alternatively, any known size that can be integrated into a medical device can be used. In a further alternative, the actuators can be any known actuators used in medical devices to actuate movement or action of a component. Examples of motors that could be used for the motors described herein include the EC 10 BLDC+GP10A Planetary Gearhead, EC 8 BLDC+GP8A Planetary Gearhead, or EC 6 BLDC+GP6A Planetary Gearhead, all of which are commercially available from Maxon Motors, located in Fall River, Mass. There are many ways to actuate these motions, such as with DC motors, AC motors, permanent magnet DC motors, brushless motors, pneumatics, cables to remote motors, hydraulics, and the like.

In these implementations, the robotic device 10 and camera 12 are both connected to the surgeon console using a cable: the robot cable 8A and camera cable 8B. Alternatively, any connection configuration can be used. In certain implementations, the system can also interact with other devices during use such as a electrosurgical generator, an insertion port, and auxiliary monitors.

As shown in FIG. 1B, the camera 12 comprises a camera latch 32 and insertion 34 and retraction 36 controls or buttons. The robotic device 10 is supported by a support arm 4 that is clamped to the operating table (shown in FIG. 1A at 2). In these implementations, a robot clamp 150 is used to connect the support arm 4 to an acceptance ring 11 on the robot handle or body 10A.

According to the implementations of FIG. 1B and FIG. 2A, the arms 14, 16 each have active degrees of freedom and an additional active joint 14F, 16F to actuate the end effectors, or tools 18, 20. It is understood that more or less degrees of freedom could be included. The device in this implementation has a connection line 8 (also referred to as a "pigtail cable") (partially shown) that includes electrical power, electrocautery, and information/communication signals. In certain implementations, the device has distributed control electronics and software to help control the device 10. Some buttons can be included to support insertion and extraction of the device into and out of the abdominal cavity. In this implementation, the integrated camera 12 is also shown inserted in the device body 10A. When inserted into the body 10A, the camera 12 has a handle or body 12A that extends proximally from the proximal body end 10C and a flexible camera imager 12B extending from the distal body end 10B.

Figure 2B:
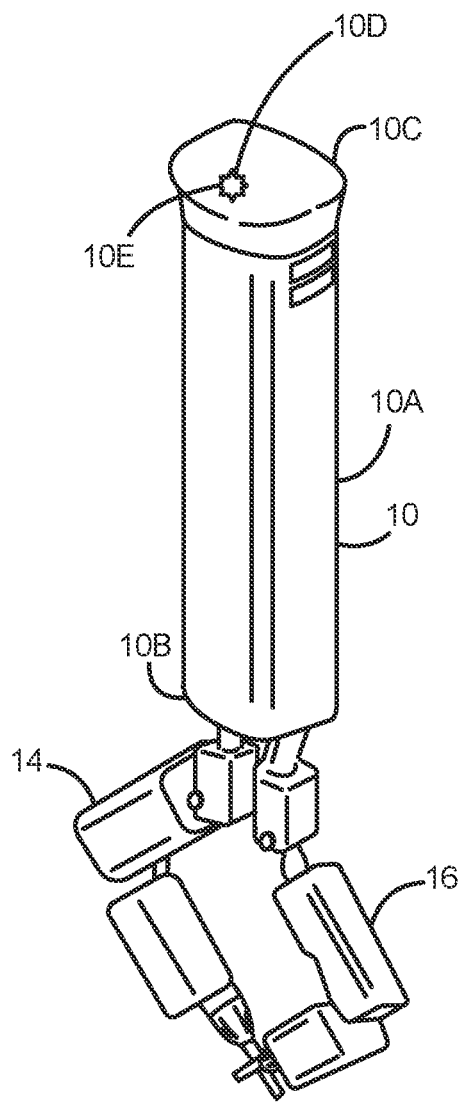
FIG. 2B is a three-quarters perspective view of the robot of the implementation of FIG. 2 without the camera.
Figure 2C:
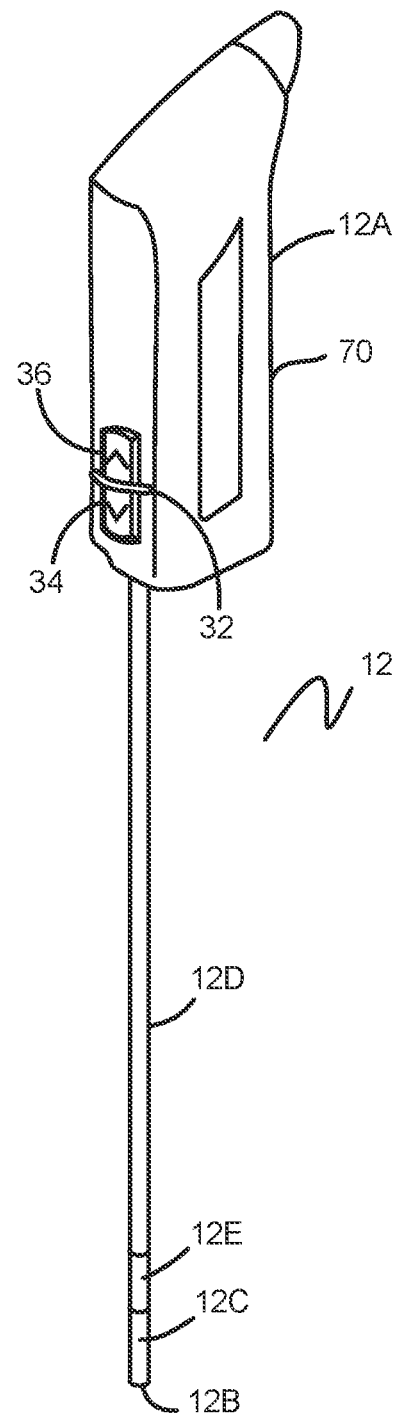
FIG. 2C is a three-quarters perspective view of the camera of the implementation of FIG. 2 without the robot.

FIGS. 2B and 2C depict the robotic device 10 with the camera assembly 12 removed, according to one implementation. In these implementations, and as shown in FIG. 2 and FIGS. 3-4, the camera imager 12B is designed to be positioned between the two arms 14, 16 and capture that view between the two arms 14, 16. In these implementations, the camera 12 extends through the robot body 10A such that the camera imager 12B exits near the joints between the body and the robotic arms (the "shoulder" joints 14A, 16A). The camera 12 has a flexible, steerable tip 12C to allow the user to adjust the viewing direction. The end effectors 18, 20 on the distal end of the arms 14, 16 can include various tools 18, 20 (scissors, graspers, needle drivers and the like). In certain implementations, the tools 18, 20 are designed to be removable by a small twist of the tool knob that couples the end effector to the arm 14, 16.

As is shown in FIGS. 2B and 2C, the camera assembly 12 has a handle 12A and a long shaft 12D with the camera imager 12B at the distal tip 12C. In various implementations, the flexible tip 12C and therefore camera imager 12B can be steered or otherwise moved in two independent directions in relation to the shaft 12D at a flexible section 12E (black section on shaft) to change the direction of view. In certain implementations, the camera 12 has some control buttons 12F as shown. In some implementations, the camera assembly 12 can be used independently of the robotic device 10 as shown in FIG. 2C.

Alternatively, the assembly can be inserted into the robotic device 10 though a lumen 10D defined through the body 10A of the robotic device 10 as shown. In certain implementations, the lumen 10D includes a seal/port 10E to ensure that the patient's cavity remains insufflated (as shown in relation to FIG. 1B). According to one implementation, the robotic device 10 can have a sensor to determine if the camera is positioned in the camera lumen 10D of the device 10.

Figure 11A:
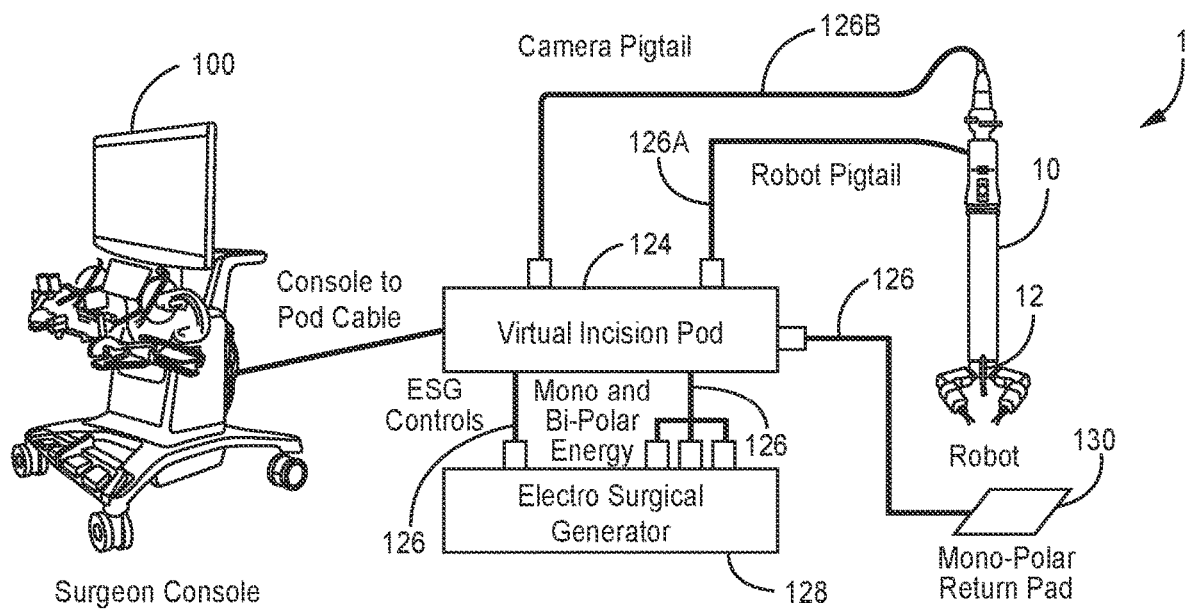
FIG. 11A is a schematic view of the robot, pod and console, showing the schematic connection maps between the components, according to one implementation.
Figure 11B:
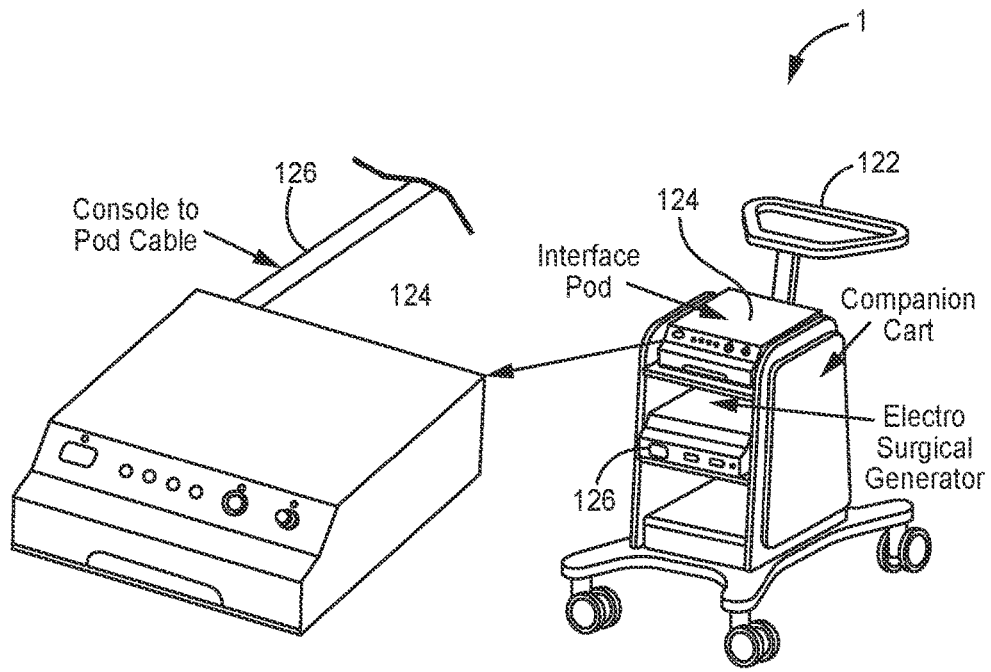
FIG. 11B is a perspective pop-out view of the interface pod on the support cart, according to one implementation.

In use, the distal portion of the robotic device 10 is inserted inside the body of the patient. Thereafter, the robot and camera can both be controlled by the surgeon via the surgeon console sitting outside the sterile field. The surgeon console has user input devices (i.e. joysticks) that allow the surgeon to control the motion of the robot, as described in detail below. There are also pedal inputs and a touchscreen that control device 10 functions in certain implementations, as shown in FIGS. 11A-11B. The console can have a main display that provides images of the surgical environment via the robot camera.

It is understood that in the described implementations, the robotic device 10 has a pair of miniaturized human-like arms 14, 16 attached to a central body or handle 10A, as shown in FIG. 1B, FIG. 2A, FIG. 2B and FIG. 3A and FIG. 3B. Alternatively, any in vivo robot can be utilized with the system implementations disclosed or contemplated herein.

The robot handle 10A in the implementation of FIGS. 1B-3B has a lumen 10D (shown in FIG. 2B) and docking feature that allows the camera 12 to be inserted and removed from the body 10A while maintaining abdominal insufflation. When inserted (as shown in FIGS. 1B and 2A), the camera 12 has an articulating tip 12B that can include a light source and allows the surgeon to view the surgical tools 14, 16 18, 20 and surgical environment.

In these implementations, the camera 12 can be locked in place and can be removed using a latch button 32 on the camera handle 12A or elsewhere. In these implementations, the surgical robotic device is supported by a support arm 4 that is clamped to the operating table 2. As described in relation to FIGS. 15 and 16, a robot clamp is used to connect the support arm to an acceptance ring on the robot handle. Alternatively, the robotic device 10 can be supported via any known support component.

Figure 3A:
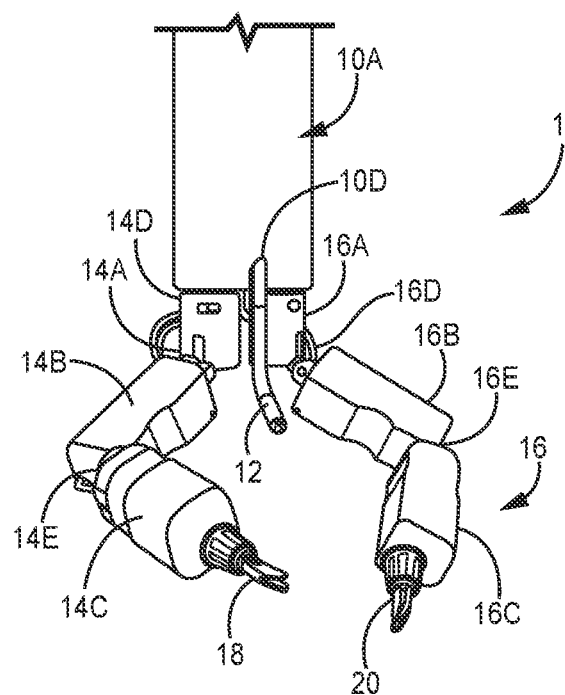
FIG. 3A is a close-up three-quarters front view of the robotic device with an engaged positionable camera, according to one embodiment.
Figure 3B:
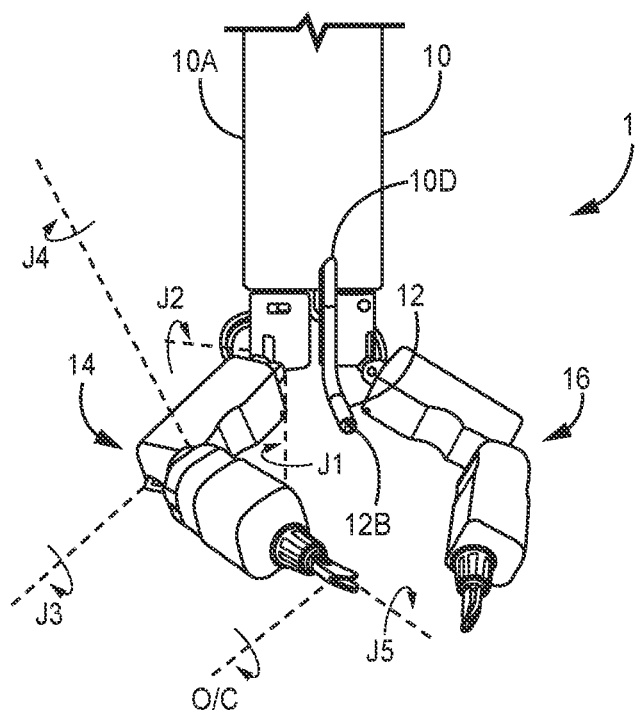
FIG. 3B is a close-up three-quarters front view of the robotic device with an engaged positionable camera showing the degrees of freedom of the arms, according to one embodiment.

As shown in FIG. 3A and FIG. 3B, in use, after the camera 12 is inserted into the robot body 10A, the distal tip of the camera 12 passes through a lumen in the robot and extends into the surgical environment. The distal tip 12B of the camera 12 can then be actuated to provide views of the surgical tools and surgical target. It is understood that the camera 12 can be used with any similar robotic device having a camera lumen defined therethrough.

Each robot arm 14, 16 in this implementation has six degrees of freedom, including the open/close function of the tool, as shown in FIG. 3B. The robot shoulder is approximately a spherical joint similar to a human shoulder. The shoulder can yaw (J1), pitch (J2), and roll about the upper arm segment (J3). These first three axes of rotation roughly intersect at the shoulder joint. The robot elbow (J4) allows rotation of the forearm with respect to the upper arm. Finally, the tool can roll (J5) about the long axis of the tool and some tools have an open/close actuation function. In contrast, it is understood that a hook cautery tool does not open/close.

Figure 4A:
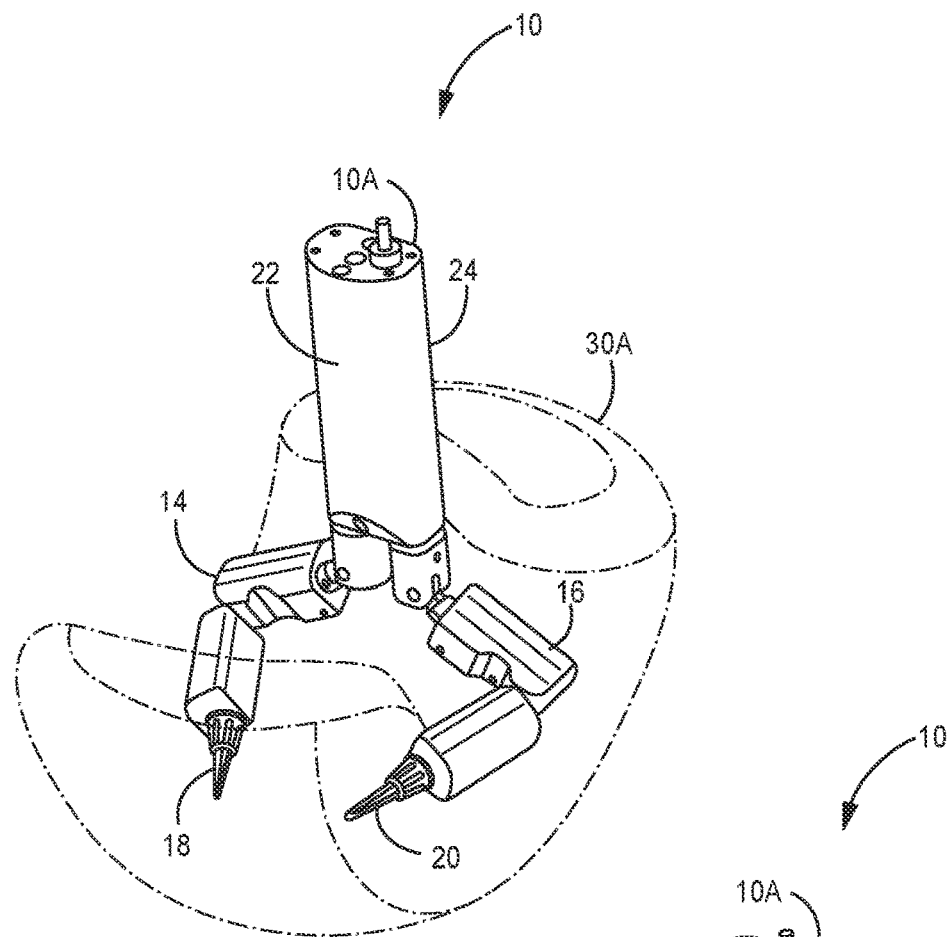
FIG. 4A is a perspective view of a surgical device showing various workspaces for one arm, according to one embodiment.
Figure 4B:
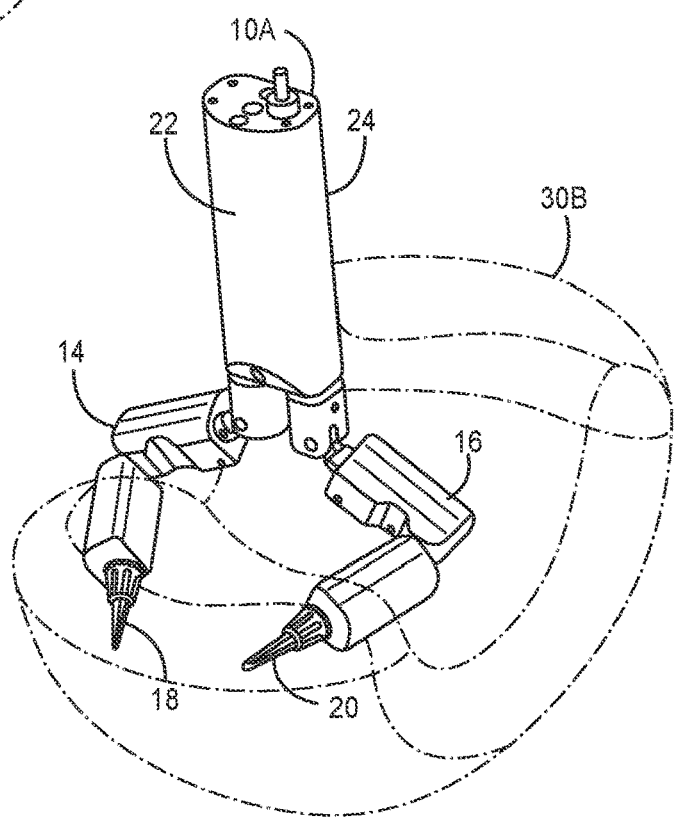
FIG. 4B is a further perspective view of the surgical device of FIG. 6A, showing the workspace of the other arm.

The surgical robot in this implementation has significant dexterity. As shown in FIG. 4A and FIG. 4B, the six degrees of freedom described above allow the robot's arms 14, 16 to reach into the confined spaces of the abdominal cavity.

Figure 5:
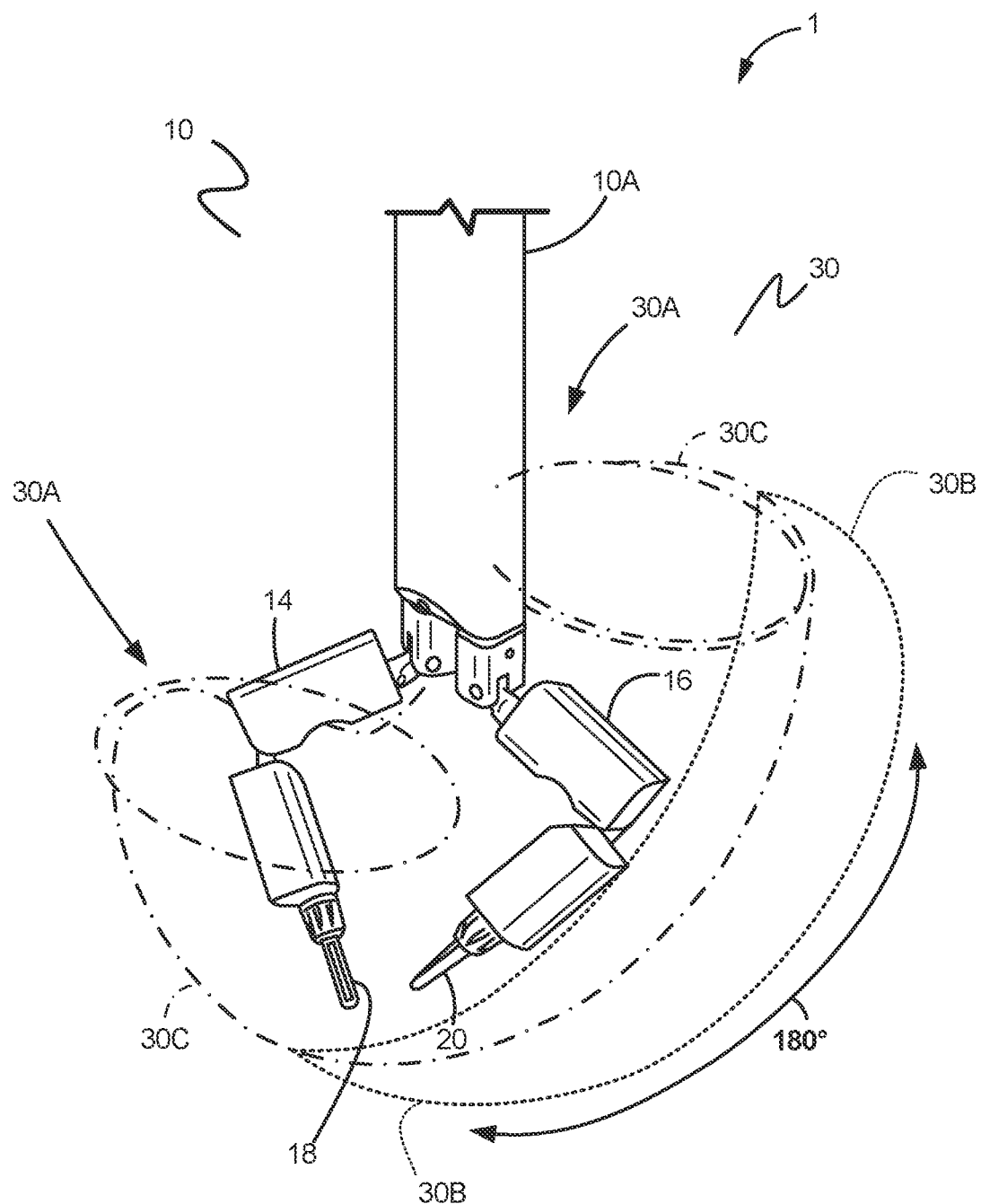
FIG. 5 is a perspective view of a surgical device showing various workspaces for the arms, according to one embodiment.

FIGS. 4A, 4B, 5 and schematically depict the entire workspace 30 as well as the individual reachable workspaces 30A, 30B of each of the arms 14, 16 of a robotic device 10, according to certain implementations. In these implementations, "workspace" 30 means the space 30 around the robotic device 10 in which either arm and/or end effector 18, 20 can move, access, and perform its function within that space.

FIG. 5 shows the regions that can be reached by the left arm and by the right arm. More specifically, FIG. 5 depicts a perspective view of the device body 10A and further schematically shows the entire workspace 30 as well as the individual workspaces 30A, 30B of the first arm 14 and second arm 16, respectively. Note that the each arm 14, 16 has a range of motion and corresponding workspace 30A, 30B that extends from the front 22 of the device to the back 24 of the device 10. Thus, the first arm 14 equally to the front 22 and the back 24, through about 180° of space relative to the axis of the device body 10A for each arm 14, 16. This workspace 30 allows the robotic device to work to the front 22 and back 24 equally well without having to reposition the body 10A. The overlap of these volumes represents a region that is reachable by both the left and right arms and is defined as the bi-manual robot workspace. The surgeon will have full robot dexterity when working in this bi-manual region.

Figure 6:
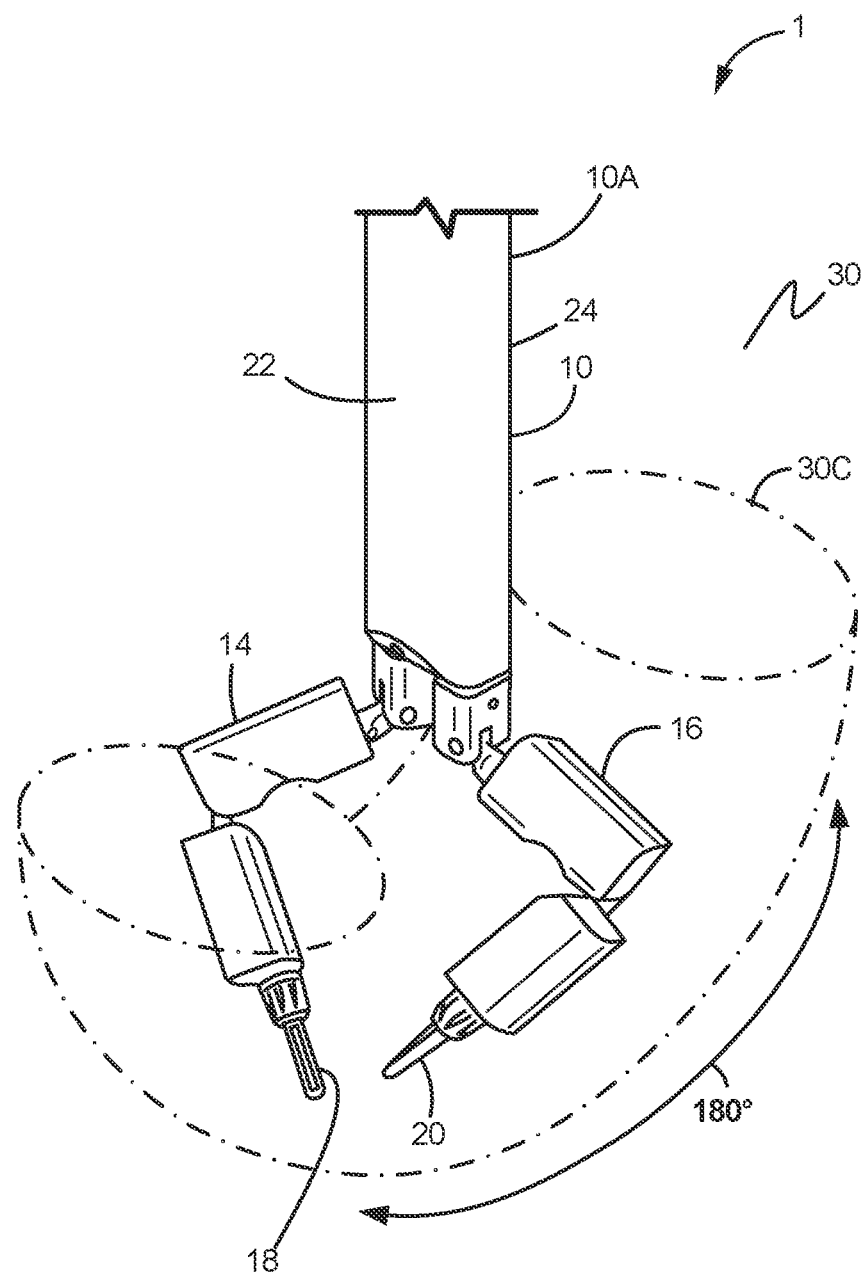
FIG. 6 is a further perspective view of the surgical device of FIG. 6A, showing the workspace of one arm.

As best shown in FIG. 6, the overlap of the ranges of motion for the individual arms in these implementations also enables an intersecting, or bi-manual workspace 30C (as is also shown in FIG. 6A). It is understood that the intersecting workspace 30C in these implementations encompasses the workspace 30C reachable by both arms 14, 16 and end effectors 18, 20 in any individual device 10 position. Again, in these implementations, the intersecting workspace 30C includes a range of about 180° of space relative to the axis of the device body 10A.

The bi-manual workspace 30C is approximated by an ellipse that is rotated 180 degrees about the shoulder pitch joint (J2 in FIG. 3B) and is shown in FIG. 6. For one design, the ellipse is approximately 4.5" (11.5 cm) on the long axis and 3.25" (8.25 cm) on the minor axis. The bi-manual workspace 30 extends from in front of the robotic device 10 to below the robot and is also behind the back of the robot. This dexterity of the robotic arms 14, 16 allows the surgeon to operate the arms 14, 16 to work equally well anywhere inside this bi-manual workspace 30C.

In addition, according to this implementation, the surgical robotic device 10 can reach any area of the abdominal cavity because it can be easily repositioned during the procedure via "gross positioning." That is, the device 10 can be quickly, in a matter of seconds, be moved by adjusting the external support arm 4 and robot clamp 150. The combination of gross positioning of the robotic device 10 and the dexterity of the robot arms 14, 16 allow the surgeon to place the device 10 so it can work anywhere in the abdominal cavity with the arms 14, 16 well triangulated for the given procedure, as discussed below.

Figure 7:
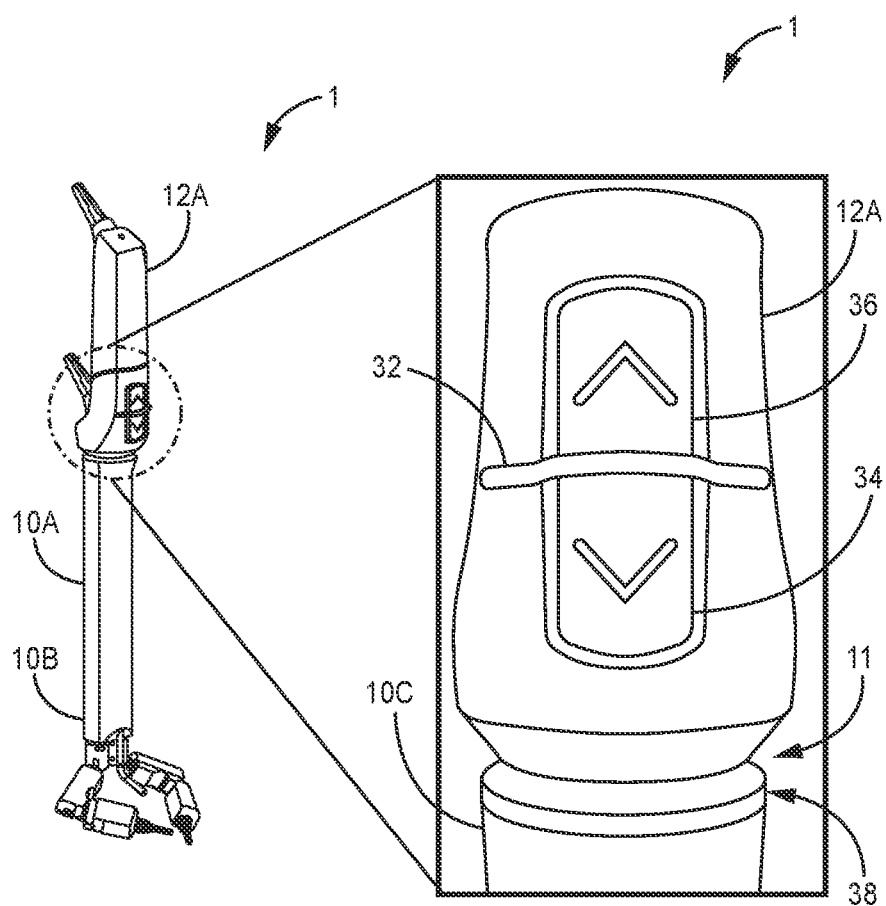
FIG. 7 is a zoomed in view of the camera operations system showing the components on the camera handle, according to one embodiment.

Turning to the insertion of the device 10 and camera 12 in greater detail, FIG. 7 depicts a detailed view of the handle 12A according to certain implementations. In FIG. 7, the camera 12 has a camera latch 32 and insertion 34 and retraction 36 controls or buttons. The robotic device 10 is supported by a support arm 4 that is clamped to the operating table (shown in FIG. 1A at 2). In these implementations, a robot clamp 150 is used to connect the support arm 4 to an acceptance ring 154 on the robot handle or body 10A.

In various implementations of the system 1, the device 10 is inserted into the abdomen of the patient by executing a series of configurations and/or arm positions. In certain implementations, the insertion 34 and retraction 36 controls or buttons allow the physician or user to executed the respective insertion and retraction steps/positions through the insertion and/or retraction, as would be understood. Further, in certain implementations, the camera latch 32 toggles the internal components of the device 10 and/or camera 12 into "locked" or "unlocked" positions, thereby securing the camera 12 within the device 10 or allowing it to be freely removed from the camera lumen, as would be understood.

Various implementations of the surgical robotic device 10 according to these implementations have an indicator light 38 or lights 38 disposed at the proximal end 10C of the device 10 and constructed and arranged to indicate any state of the device and can be any color or any intensity or of varying intensity. In certain implementations, LED lights or similar lighting components can be used, as would be appreciated by those of skill in the art.

In various implementations, the robotically articulated camera 12 is part of a system 1 to provide visual feedback to the surgeon from the perspective of the camera 12. In one specific implementation, the camera provides 1080 p 60 Hz. digital video. Alternatively, the camera can provide any known video quality.

Figure 8A:
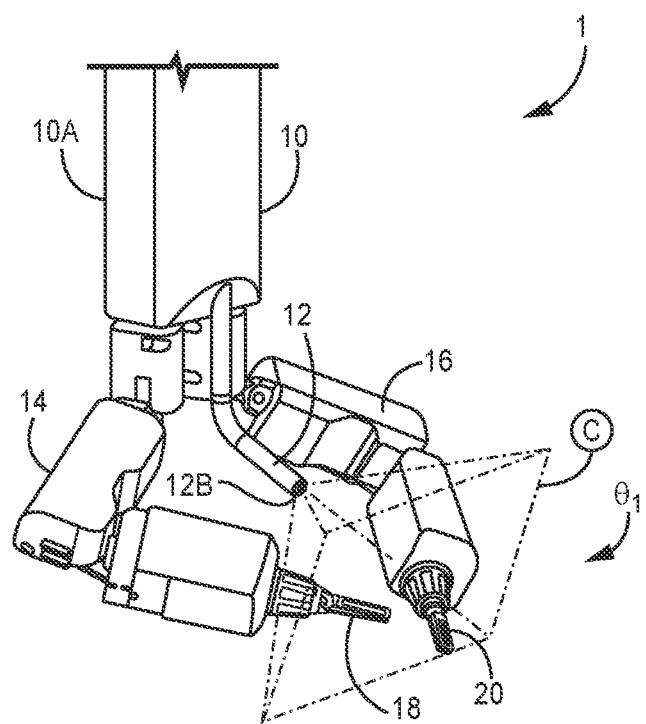
FIG. 8A is perspective three quarters view of the surgical robotic device and positionable camera showing the camera field of view, according to one implementation.

As is shown in the implementation of FIG. 8A, the camera 12 is constructed and arranged to be inserted into a lumen in the robot base link as shown in FIG. 1 so that the tip 12B of the camera is always positioned between the two robot arms 14, 16, and that the camera 12 has a field of view (shown with reference letter C in FIG. 8A).

It is likewise understood that when the robotic device 10 is repositioned during surgery, the camera 12 and robotic device 10 can move together or in a coordinated fashion in this configuration. This results in coordinated triangulation between the robot and tools 18, 20 for any configuration, positioning, and use of the device 10.

In accordance with certain implementations, the camera 12 is designed to visualize all possible positions of the robot's tools 18, 20. Accordingly, the camera tip 12B can be robotically articulated as to reposition the field of view (C). It is understood that in certain implementations, the surgeon controls this movement via the surgeon console 100 (described in detail in relation to FIG. 11A and FIG. 11B).

Figure 8B:
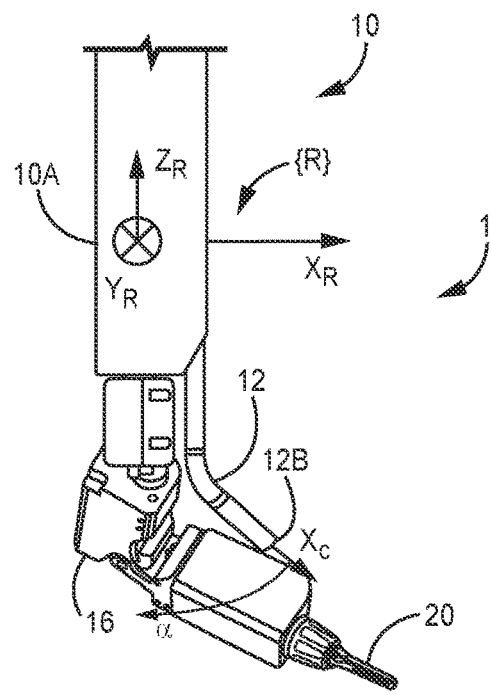
FIG. 8B is a cutaway side view of the robotic surgical device comprising a positionable camera and showing a first degree of freedom, according to one embodiment.
Figure 8C:
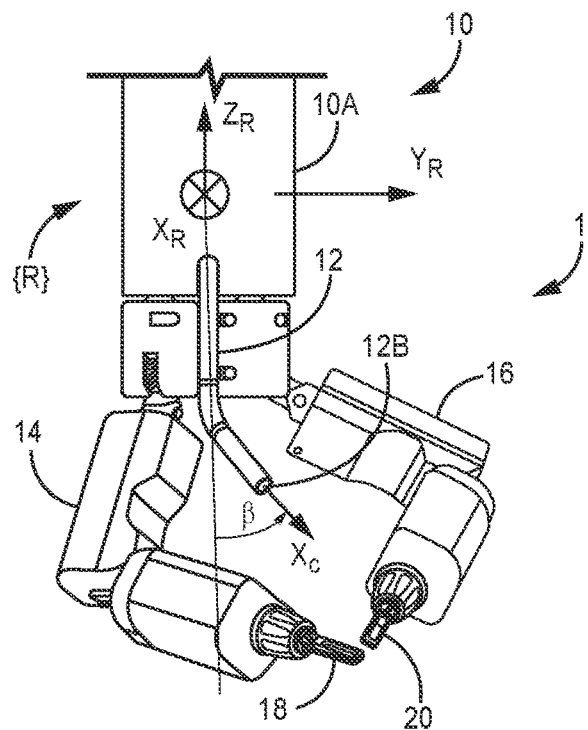
FIG. 8C is a cutaway side view of the robotic surgical device comprising a positionable camera and showing a second degree of freedom, according to one embodiment.

As shown in the implementations of FIG. 8B and FIG. 8C, the camera 12 can move in pitch (screen up/down) and/or yaw (screen left/right), respectively, which may also be referred to as tilt and pan, respectively. In certain implementations, the system uses an articulating camera 12, as has been previously described. Briefly, in these implementations, the camera 12 articulates to ensure the surgeon can view all possible locations of the robot arms 14, 16 as well as the desired areas of the surgical theater.

As mentioned above, the approximate camera field of view (C) for a given location of the camera is shown in the implementation of FIG. 8A. The camera field of view (C) is about 100 degrees in this implementation, as defined by the angle $\theta_1$ created along the diagonal of the cross section of a rectangle. Any other known field of view angle can be used. It is appreciated that many other angles are possible. In these implementations, it is understood that the surgeon/user is able to view both robot end effectors 18, 20 over a wide range of working distance.

Further, as the robotic device 10 makes large motions with its arms 14, 16—like those described in FIGS. 5 & 6—the robot camera tip 12B can be moved using active joints in coordination with the large arm movements to view the entire robot workspace. In certain implementations, the joints of the camera are actively controlled using motors and sensors and a control algorithm implemented on a processor.

The system 1 according to certain implementations has a processor constructed and arranged to execute such a control algorithm. The control algorithm can be provided on computer-readable medium on a processor optionally having an operating system, memory, an input/output interface and the like, as would be appreciated by one of skill in the art. The processor in various implementations can be disposed in the camera handle 12A, device body 10A, in the surgical console 100 or elsewhere, as would be appreciated by those of skill in the art. For purposes of the discussed implementations, the processor is located inside the surgical console 100 as would be readily appreciated.

In these implementations, the control algorithm allows for automated and/or semi-automated positioning and re-positioning of the camera 12 about the pitch ($\alpha$) and/or yaw ($\beta$) rotations shown in FIGS. 8B and 8C, relative to the robotic device 10. This 2 degrees-of-freedom (DOF) system can also be constructed and arranged to translate the camera tip 12B as the robotic device 10 articulates. It is understood that alternative designs are possible.

Figure 8D:
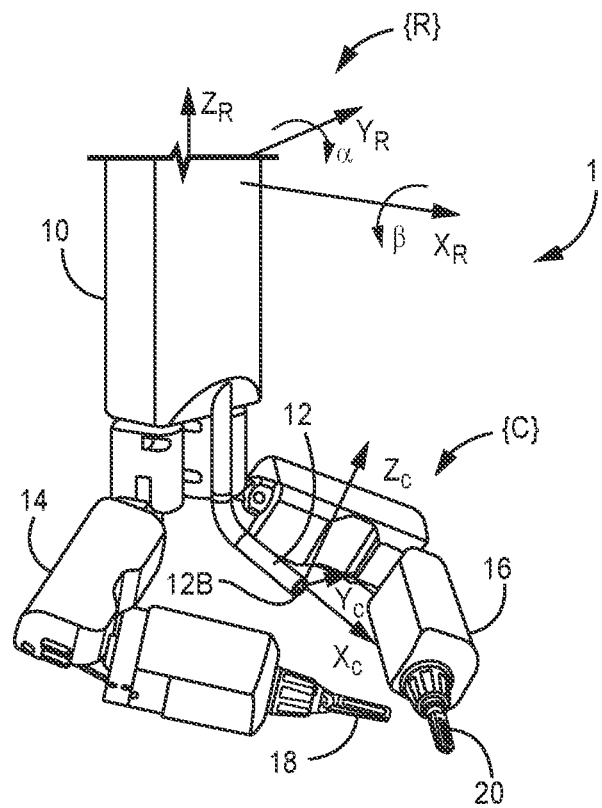
FIG. 8D is a perspective three-quarters side view of the robotic surgical device comprising a positionable camera and showing coordinate reference fames, according to one embodiment.

In the implementation of FIG. 8B and FIG. 8C, the system 1 executes a control algorithm such as an algorithm as discussed above. According to these implementations, the camera 12 is capable of rotating relative to the robot body 10A so as to direct or "point" the camera 12 in various directions to alter the field of view. In this implementation, a robot coordinate frame {R} is affixed to the robot body 10A and is defined by orthogonal unit vectors xR, yR, and zR. A camera coordinate frame {C} is defined with relation to the location of the imaging tip 12B of the camera. In this implementation, the {C} frame is defined by the orthogonal unit vectors $x_C$, $y_C$, and $z_C$, as shown in FIGS. 8B-8D.

In this implementation, the $x_C$ axis is located so as to extend outward from the imaging tip 12B as an extension of the longitudinal axis of the camera 12 and thus point directly in line with the field of view of the camera 12 (as shown in FIG. 8A at C). The $y_C$ axis points directly to the left of the camera image and the $z_C$ axis is vertical when viewed by the camera imager. The {C} frame is shown from the perspective of the camera in FIG. 8E.

In this implementation, two angles are defined to describe the 2 DOF rotation of the camera frame {C} relative to the robot frame {R}; first angle $\alpha$ and second angle $\beta$. Many angles can be used, but in this representative implementation, fixed angles are used and are described by rotations about the xR and $y_R$ frames.

The first angle $\alpha$ is defined as a rotation of the camera tip 12B ($x_C$ axis) relative to the xR axis about the $y_R$ axis, as is shown in FIG. 8B. The second angle $\beta$ is defined as a rotation of the camera tip 12B ($x_C$ axis) relative to the $y_R$ axis about the xR axis, as is shown in FIG. 8C.

In these implementations, the system can generate coordinate transformations from one of the camera frame {C} and/or the robot frame {R} to the other—or to any other coordinate frame.

As shown in the implementations of FIGS. 8D-8I, the system 1 according to certain implementations can be constructed and arranged to execute a control algorithm and move the camera 12 and arms 14, 16 in response to the defined camera frame {C} and/or the robot frame {R}. That is, it is understood that in certain implementations, the surgeon or user commands robotic device 10 motion based on images returned by the camera 12, and that the system 1 is constructed and arranged to adjust the locations of various reference frames and components, as described herein.

According to certain of these implementations, the camera frame {C} is fixed to the camera tip 12B so it does not move relative to the view provided by the surgeon.

Figure 8E:
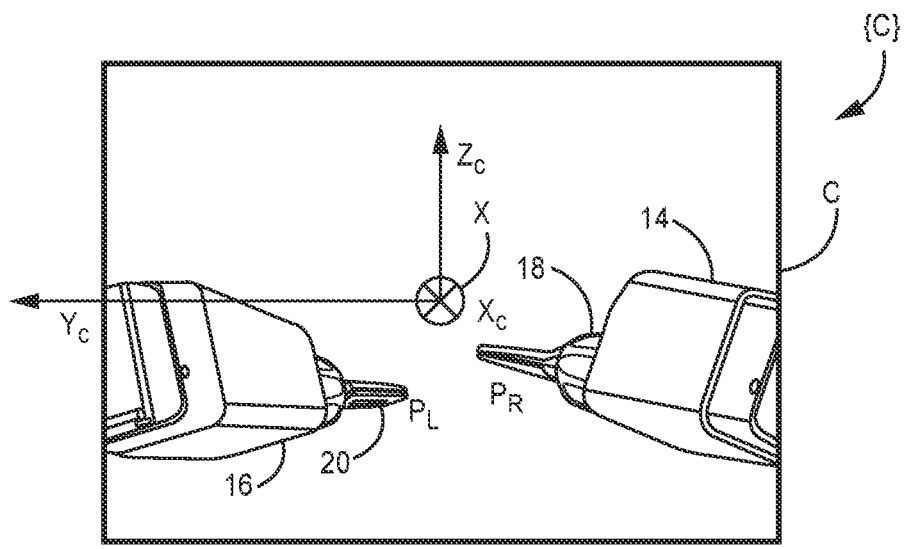
FIG. 8E is a view from the perspective of the positionable camera inserted into the robotic surgical device and showing the end effectors within that field of view, according to one embodiment.

As shown in FIG. 8E, the system 1 according to these implementations establishes an origin (shown at X) of the camera frame {C} at the intersection of the xc-yc- and zc-axis. Likewise, the robot frame {R} establishes a reference point or origin relative to the position of the device components for coordinated translation between the frames {C}, {R}, as would be understood.

Continuing with the implementation of FIG. 8E, the locations $\underline{P}_L$ and $\underline{P}_R$ of the end effectors 18, 20 can then be located within the camera frame {C}. The location of the end effectors 18, 20 is known in the robot frame {R} as that is what is controlled to operate the robot. Then a coordinate transformation is established between the {R} frame and the {C} frame to locate the position of the end effectors 18, 20 in the camera frame.

It is understood that the positioning of the camera 12 according to these implementations can be controlled and/or planned using several approaches. One approach is to allow the user to control the position of the camera 12 via an input device operably coupled to the console 100, and as described in detail in relation to FIG. 11A and FIG. 11B. Some non-limiting examples of the input device include, for example, a hand or foot controlled joystick. Further implementations have independent joystick-like devices that control the various motions—for example pitch $\alpha$ and yaw $\beta$—of the camera. A further approach includes toggling the function of one of the robot hand controllers and/or pedal to then temporarily use the hand controller to command the motion of the camera 12.

In further alternate implementations, additional data relating to the position of the camera 12 and other components such as the arms 14, 16 can be used to establish the reference frames {R}, {C} to choose the direction of the camera 12. These implementations can include end effector 18, 20 positions and velocities as well as many factors associated with the motion of the tools, as would be appreciated by those of skill in the art.

Figure 8F:
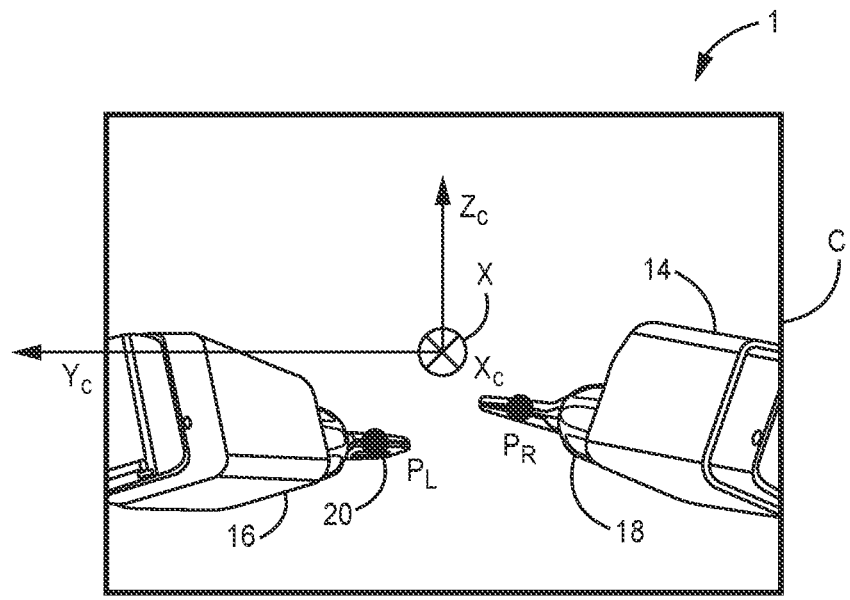
FIG. 8F is a view from the perspective of the positionable camera inserted into the robotic surgical device and showing the locating of the end effectors within that field of view and generating an origin, according to one embodiment.

A further approach according to certain implementations is to control the movement of the camera 12 to be fixed on the end effectors 18, 20. When viewed from the camera perspective C according to these implementations, the end effector 18, 20 locations are defined as $\underline{P}_L$ and $\underline{P}_R$, where $\underline{P}_L$ and $\underline{P}_R$ are vectors containing the x, y, and z coordinates of the location of the respective points. These can be detected via the camera 12 and their position can be established in the camera frame, as is shown in FIG. 8D, FIG. 8E and FIG. 8F.

Figure 8G:
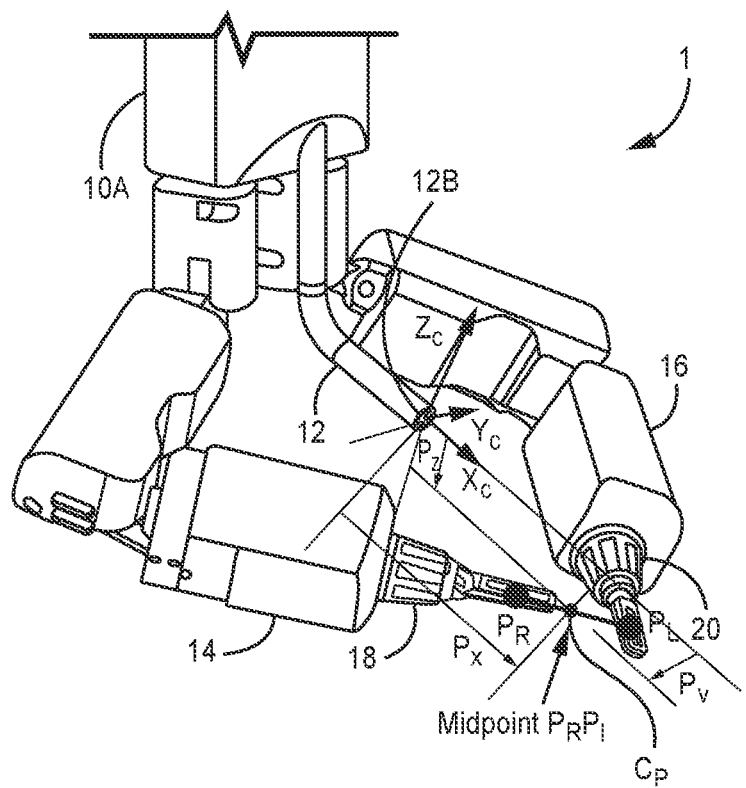
FIG. 8G is a perspective three-quarters side view of the robotic surgical device comprising a positionable camera and showing coordinate reference fames and the generation of midpoint calculations, according to one embodiment.

In various of these implementations, it is therefore possible to calculate the midpoint Midpoint $\underline{P}_L\underline{P}_R$ between the end effectors in the camera frame FIG. 8G. In these implementations, a line is created between the left 16 and right 18 end effector locations $\underline{P}_L$ and $\underline{P}_R$, as is shown in FIG. 8G. The midpoint of that line $^C\underline{P}$ can then be located in the camera coordinate frame—or in any other frame using known coordinate transformation matrices—where:

$$c_P = \text{Midpoint } \underline{P}_R\underline{P}_L = \begin{bmatrix} P_x \\ P_y \\ P_z \end{bmatrix}$$

Figure 8H:
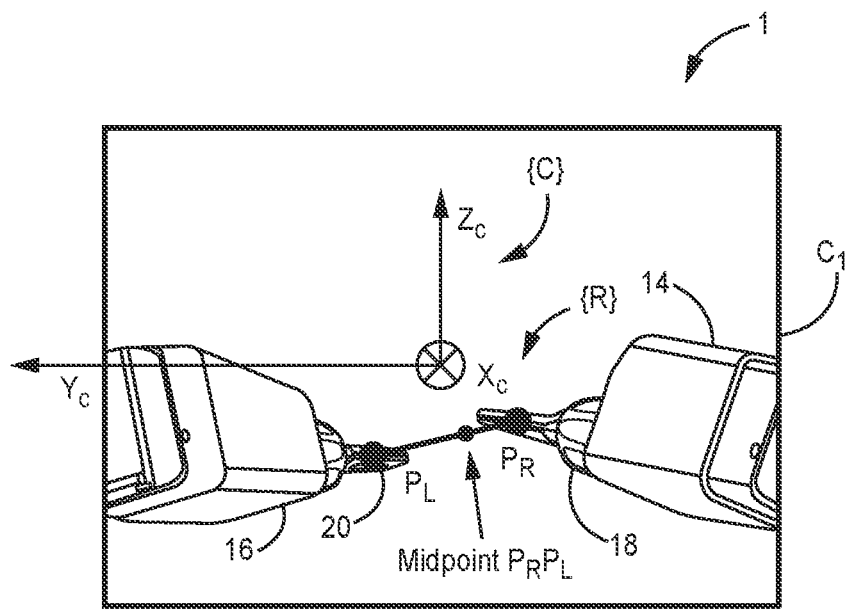
FIG. 8H is a view from the perspective of the positionable camera inserted into the robotic surgical device and showing the end effectors within that field of view and midpoint, according to one embodiment.

Using these reference frames, it is possible to re-position an initial camera view $C_1$ to a second camera view $C_2$ via coordinate transformations to ensure the camera 12 remains centered on the tools 18, 20. For example, as is shown in FIG. 8H, when viewed from the initial camera view $C_1$, the {R} midpoint $\underline{P}_R\underline{P}_L$ can be observed relative to the camera coordinate frame {C}. It is understood that the {C} reference frame origin $X_c$ is not aligned with the midpoint $\underline{P}_R\underline{P}_L$ established by the {R} reference frame.

Figure 8I:
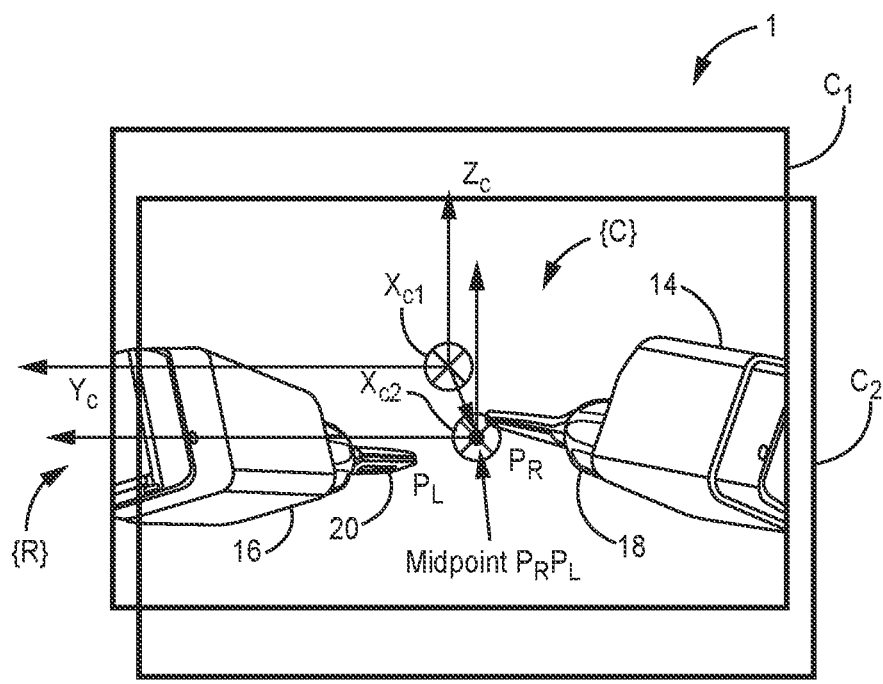
FIG. 8I is a view from the perspective of the positionable camera inserted into the robotic surgical device and showing the re-positioning of the camera, according to one embodiment.

The camera 12 can then be re-positioned so as to zero the origin point $X_c$ of the camera to the midpoint $\underline{P}_R\underline{P}_L$ of the two tools 18, 20 via coordinate transformations, as is shown in FIG. 8I at $X_{C1} \rightarrow X_{C2}$. This motion can also be damped. In these implementations, the system 1 retards the motion of the camera tip 12B by reducing the motion of the tip with a term proportional to the velocity of the tip, as would be understood.

Further implementations involving the control of camera 12 utilize a running average position of each right 18 and left 20 end effector is calculated. In these implementations, the difference between average position and actual position is calculated for each arm 14, 16. If the difference is greater than a threshold value, the arm is considered to be moving. In these implementations, camera actuation outputs are calculated via the kinematics of the camera as compared with a target position. When only one arm is moving, the target position is the position of only the moving arm. If both arms are moving, the midpoint between the two end-effector positions is used as the target position, as would be understood.

In implementations such as these running-average kinematic control execute pseudo-code such as:

```
algorithm kinematics is
   input: point at which to aim camera, pos
   output: camera angles to point camera at pos, theta1, theta2, . . .
   set theta1, theta2, . . . based on camera kinematics and pos
   return theta1, theta2, . . .
algorithm cameraTracking is
   input: left and right end effector positions, posL & posR
   output: camera actuation angles, theta1, theta2, . . .
   enqueue posL into FIFO array of fixed size, arrayL
   set avgL to average of arrayL
   set diffL to difference of avgL & posL
   enqueue posR into FIFO array of fixed size, arrayR
   set avgR to average of arrayR
   set diffR to difference of avgR & posR
   if diffL is greater than movementThreshold
      set movingL to true
   else
      set movingL to false
   if diffR is greater than movementThreshold
      set movingR to true
   else
      set movingR to false
   if movingR is true and movingL is false
      return kinematics(posR)
   else if movingL is true and movingR is false
      return kinematics(posL)
   else if movingL is true and movingR is true
      set midPos to average of posR & posL
      return kinematics(midPos)
```

Alternatively, other clinical and robotic factors can be used to determine the camera location. For example, the velocity/position and/or the velocity/position history can be considered in the commanded camera position. In constructing and arranging the system, it is understood that a tool that moves quickly, often, or constantly, or other factors could "pull" the camera toward that tool, and that a more stationary tip may not hold the camera as close.

Further, it is well appreciated that various machine learning techniques or other algorithms can be used to determine the orientation of the camera 12. This could include neural networks, genetic algorithms, or many other machine learning algorithms known and appreciated in the art.

Figure 9:
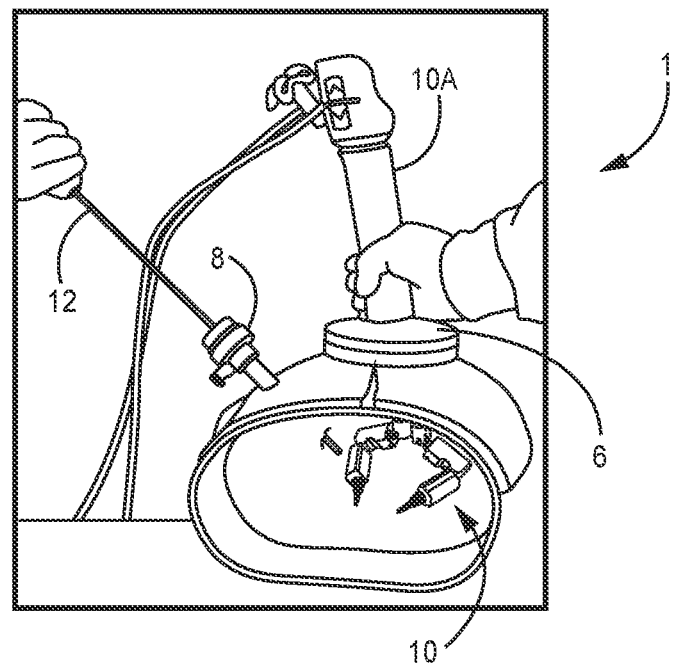
FIG. 9 is a front view of the robotic surgical system showing the robotic device with an engaged positionable camera, according to one embodiment.

Alternatively, the surgeon may also choose to remove the camera 12 from the robotic device 10 and use it in another, known laparoscopic port 8 like a standard manual laparoscope as shown in FIG. 9. It is understood that this perspective may be useful to visualize the robotic device 10 to ensure safe insertion and extraction via the main port 6. The camera 12 according to these implementations can also be removed from the robotic device 10 so the optics can be cleaned.

Figure 10A:
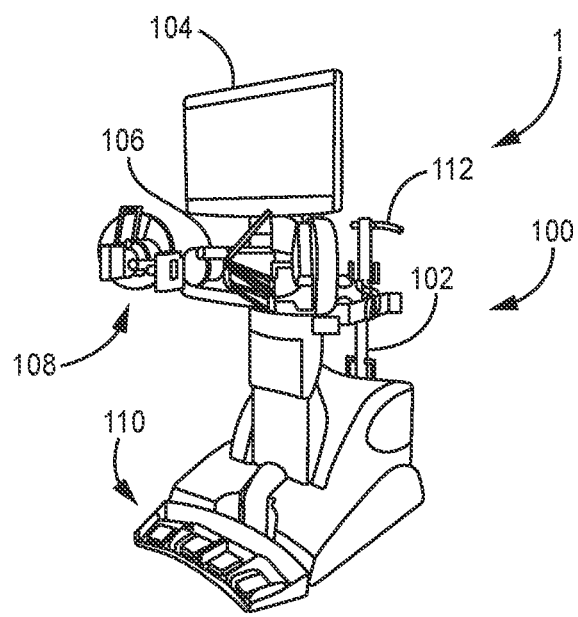
FIG. 10A is a perspective view of the surgical console, according to one implementation.

In certain implementations, the robotic device is piloted from the surgeon console 100 as shown in FIG. 10A. This exemplary implementation of the surgeon console 100 contains a main computer 102 that performs robot control functions and system monitoring. In these implementations, the surgeon views the surgical environment using the output of the robotically articulated camera shown on a high-definition real-time display 104. Several functions of the console and robot are controlled through a touch screen interface 106. The touch screen 106 is also used to display some information about the state of the robot. Alternatively, any known console can be used with the various implementations of the system disclosed or contemplated herein.

The device 10 and camera 12 motion are controlled in this implementation via the surgeon console 100 with left and right hand input devices 108. The input devices 108 interface with the surgeon's hands and monitor the surgeon's movement. As has been previously described, the input devices 108 have a surgeon presence sensor to indicate the surgeon's hands are properly engaged. The devices can also provide haptic feedback by pushing on the surgeon's hands to indicate things such as workspace boundaries and to prevent collisions between the robot arms, as was also described in the incorporated references. These input devices 108 also control open/close functions of the robot's surgical tools.

The surgeon console 100 according to these implementations can also have foot pedals 110 that are used to control various robot functions including clutching, camera movements, and various electro cautery functions. Alternatively, other input devices on the console can be used to control those various functions.

The surgeon console 100 according to these implementations is constructed and arranged to be used in either a sitting (similar to Intuitive's da Vinci) or standing position (similar to manual laparoscopy). The console 100 is designed to be easily transported between operating rooms using castors and a transport handle 112.

Figure 10B:
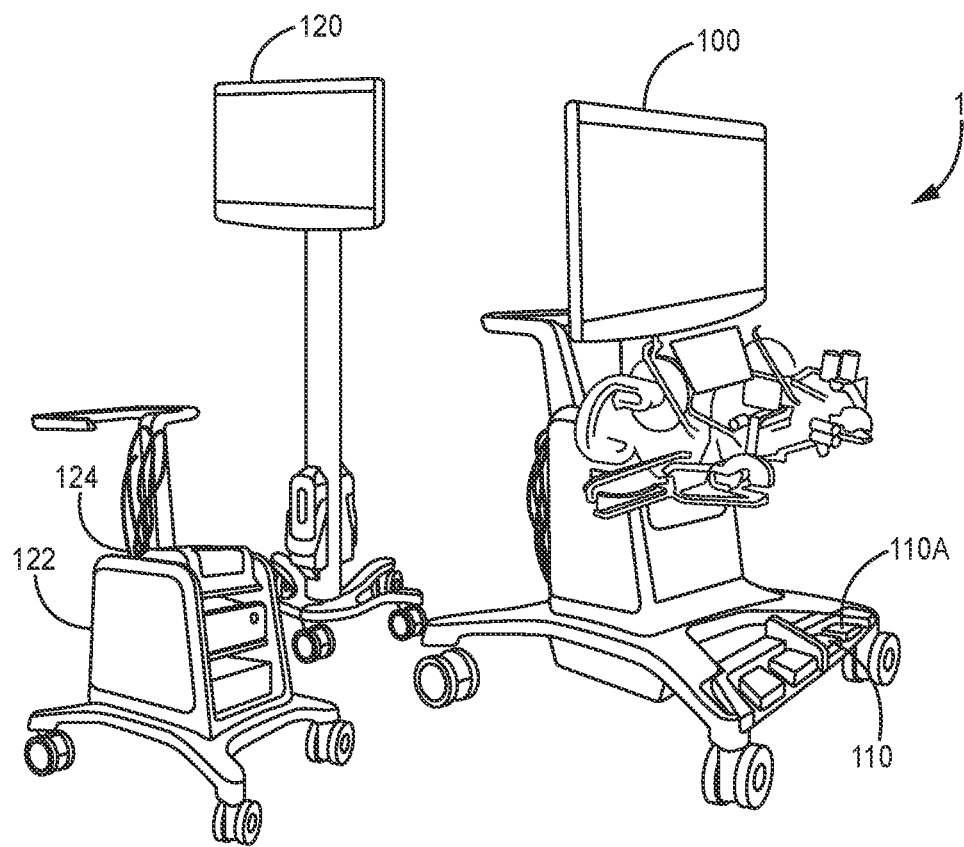
FIG. 10B is a perspective view of the surgical console, according to another implementation.

A further implementation of the surgeon console 100 is shown in FIG. 10B. In these implementations, additional, alternative support equipment is provided, here, a remote display 120 and a companion cart 122. It is understood that the space around a patient during a surgery is valuable, and that certain wired or otherwise connected components have limited range.

The remote display 120 according to these implementations is operably coupled to the other components and can be wireless or wired. This display 120 can be used to show the view from the robot camera or any other video.

In the implementation of FIG. 10B, a companion cart 122 is also provided. The cart 122 can be used to hold the robot interface pod 124 or an electro surgical generator or other equipment.

In certain implementations one 110A of the foot pedals 110 or another input device can be used as a clutch that separates coordinated motion of the hand input devices from the motion of the robot. In certain implementations, the foot pedals 110 can be configured allow the user to move the hand input devices 108 to a more desirable location in their own workspace. Then the coordinated motion can be reengaged. Alternatively, in other implementations the clutch function might separate the coordinated motion of the hand input devices from the motion of the robot and then the hand input devices might automatically move to a desired portion. Then the coordinated motion can be reengaged.

In certain system implementations, various cables 126 are used to connect the robot, camera, electrosurgical generator, and the surgeon console, as is shown in FIG. 11A.

According to one implementation, all connections of the cables 126 to and from the various system 1 components are made through a connection pod 124, shown in FIG. 10B, FIG. 11A and FIG. 11B. The cables and connectors are shown schematically in FIG. 11A.

In these implementations, the pod 124 is permanently connected to the surgeon console 100 via an approximately 20' (6 meters) cable 126 giving flexibility in the placement of the surgeon console within the operating room. Other lengths are of course possible. It is understood that in use, the pod 124 and cable 126 can be hung from the back of the console 100 for transport. When in use, the pod 124 can be placed near the electrosurgical generator and/or near the operating table.

In various implementations, the robotic device 10 and camera 12 both have pigtails 126A, 126B that are permanently attached to the robot and camera and then have connectors at the pod. The robot pigtail 126A carries electrical power and control signals as well as cautery energy. The camera pigtail 126B carries electrical power and control signals as well as a fiber optic cable for the video signal.

The pod 124 according to these implementations can also be constructed and arranged to interface with an electrosurgical generator (ESG) 128. On/Off control signals from the user at the surgeon console 100 are directly connected to the ESG 128 control inputs. The mono-polar return pad 130 is first connected to the pod 124 and then the cautery energy is routed from the ESG 128 to the appropriate surgical tools via the pod 124. In various implementations, each connection contains a sensor that allows the surgeon console to determine if connections are made correctly. This system 1 has been designed to ensure safety and simplicity of setup.

One interface pod 124 design is shown in FIG. 11B. In this implementation, the companion cart 122 is used to house the interface pod 124 and ESG 128. The interface pod connects to the surgeon console and the electro surgical unit. The interface pod 124 then has connections for the robotic device 10 and camera 12.

In various implementations, a known, commercially-available ESG 128 can interface with the system, according to one implementation. For example, in one specific implementation, the surgeon console can have two (IPX7) foot pedals 110 that open and close an electrical circuit that activates and deactivates the ESG 128. The pedals 110 are directly connected to the ESG 128. As a safety measure, the surgeon console 100 can disconnect the pedals from the ESG 128, but cannot activate the ESG 128. Activation of the ESG 128 requires the surgeon to also depress the pedals 110. Mono-polar cautery energy is delivered to the right arm of the robot and bi-polar energy is delivered to the left arm. The electrocautery energy is delivered to the surgical target through the specifically designed surgical tools—such as a grasper for bi-polar and scissors and hood for mono-polar energy. Verification testing-creepage, clearance, impedance and the like—has been performed to ensure proper interoperability function between the electrosurgical generator and the system.

Alternatively, the ESG 128 can interface with the system 1 through other input devices other than the foot pedals. Alternatively, the system has no pod 124. In addition to these specialized subsystems, certain implementations of the system can utilize one or more of the many standard general surgical and laparoscopic systems and techniques that are commonly available and provided by the users, as described below.

Further aspects of the system 1 are described herein.

Figure 12:
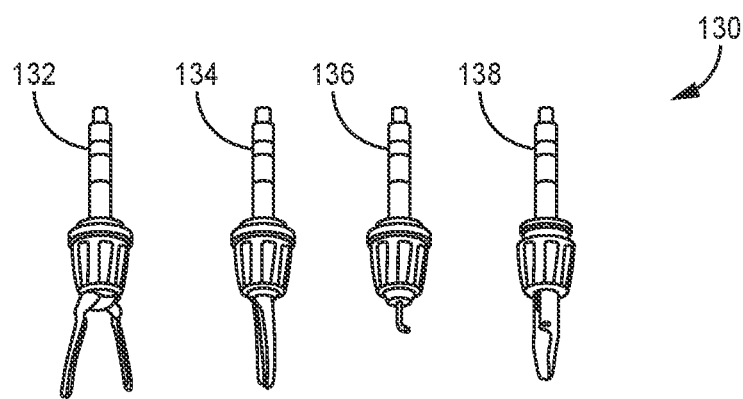
FIG. 12 is a top view of several surgical tools, according to certain embodiments.

FIG. 12 depicts views of various surgical tools (also referred to above as end effectors 18, 20) are the "hands" of the system and shown generally at 130. Four tools are shown in FIG. 12, including a fenestrated grasper 132 that is capable of bi-polar cautery, a scissors 134 that delivers mono-polar cautery, a hook 136 that delivers mono-polar cautery, and a left/right needle driver set 138. Alternatively, other end effectors can be used with the implementations disclosed or contemplated herein.

In certain implementations, these surgical instruments 130 are designed to be single-use disposable accessories to the robot system 1. They can be chosen based on clinical need for the specific surgical task.

Figure 13:
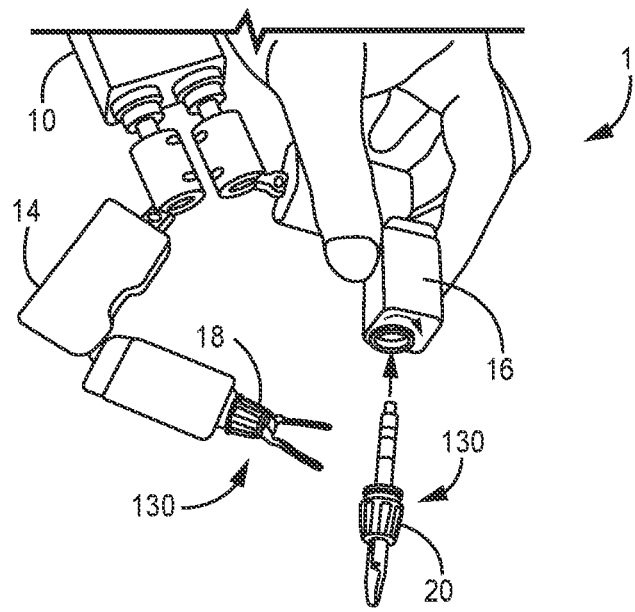
FIG. 13 is a perspective top view showing the installation of the surgical tools into the arms, according to one implementation.

The tools 130 are inserted into the distal end of the robot forearm 14, 16 and then are locked in place using a ¼-turn bayonet-style connection as end effectors 18, 20, as shown in FIG. 13. The tools 130 are removed by reversing the process. When the tools 130 are inserted they interact with connections inside the forearm to deliver cautery energy to the tool tip. Alternatively, any coupling mechanism can be used to couple any of the end effectors with the robotic device.

According to certain implementations, the surgical robotic device 10 is intended to be cleaned and sterilized for reuse. The robotic device 10 has a molded silicon protective sleeve (not shown) that covers the areas between the robot base link and the forearms. This enables the robot to be cleaned and fully exposed during the sterilization process.

Figure 14:
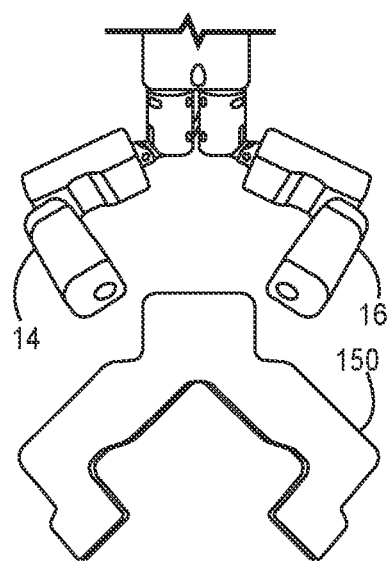
FIG. 14 is a perspective top view showing the surgical robotic device showing the sleeves, according to one implementation.

In certain implementations, protective and fitted sleeves are provided that are tailored to cover the robot arms 14, 16. One such sleeve 140 is shown in FIG. 14 prior to installation onto the robot arms 14, 16. The sleeve 140 is flexible so it does not restrict motion of the robot arms 14, 16 and is durable to tear and puncture during normal robot operation. The sleeve 140 serves as a barrier to fluid ingress into the robot. It is made of biocompatible material and, like all other tissue contact materials in the system, is compliant with ISO 10993. The robot sleeve 140 can be factory installed and stays on the robot throughout the useful life of the device 10.

The robot sleeve 140 also makes the device easily cleaned post-surgery and ensures that all patient contact surfaces are properly exposed during the sterilization process. Alternatively, any known sleeves or protective components can be used.

Figure 15:
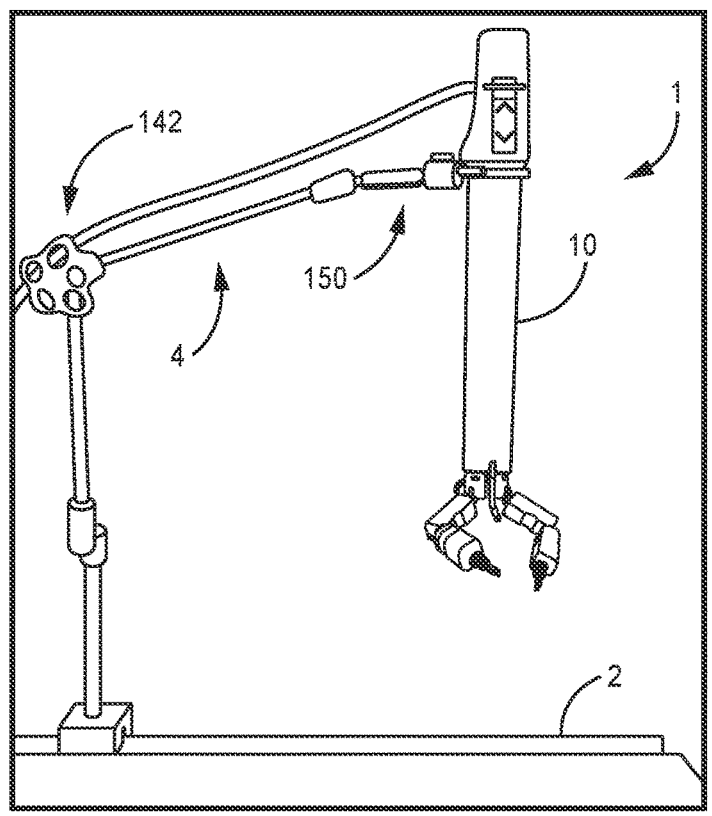
FIG. 15 is a front view of the robotic surgical system affixed via a clamp attached to a support arm, according to one implementation.

In certain implementations, a robot clamp 150 is provided to support the device 10 during the procedure. In these implementations, a known, commercially-available support arm 4 can be used to anchor the device 10 to the operating table 2, as shown in FIG. 15. It is understood that the support arm 4 has several adjustment features so it can provide stability while allowing significant repositioning of the robot. In certain examples, the support arm adjustment features are controlled using one adjustment knob 142.

Figure 16:
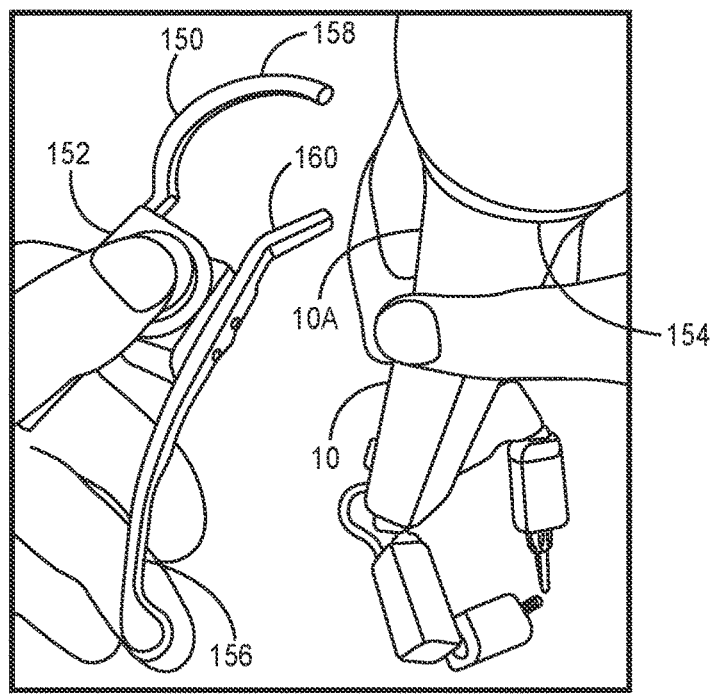
FIG. 16 is a close-up perspective view of the robotic clamp, according to one implementation.

One clamp 150 implementation is depicted in FIG. 16. The device 10 according to these implementations interfaces with the support arm 4 through a robot clamp 150 as shown in FIG. 16. The clamp 150 has a safety release button 152 that must be pressed prior to clamping or unclamping the device 10. The robot body 10A has a robot clamp interface ring 154 defined in the housing 11 to provide an interface between the clamp 150 and the device 10. After the release button 152 is pressed the robotic device 10 can be inserted or removed from the clamp 150 using the release lever 156.

In implementations such as these, the clamp 150 has a clothespin member 158 that is optionally V-grooved. The clothespin member 158 permits the smooth and controlled rotation of the device 10. In these implementations, a clasping member 160 is disposed opposite the clothespin member 158, which is urged inward to secure the device at the interface ring 154, as would be appreciated.

Although various preferred implementations have been described, persons skilled in the art will recognize that changes may be made in form and detail without departing from the spirit and scope thereof.

Although the present invention has been described with reference to preferred implementations, persons skilled in the art will recognize that changes may be made in form and detail without departing from the spirit and scope of the invention.

What is claimed is:

1. A robotic surgical system, comprising:
 a) a device body constructed and arranged to be positioned at least partially within a body cavity of a patient through an incision, the device body comprising:
  i) a first robotic surgical arm operably coupled to the device body and comprising a first end effector;
  ii) a second robotic surgical arm operably coupled to the device body and comprising a second end effector; and
  iii) a camera lumen defined in the device body;
 b) a positionable camera constructed and arranged to provide views of the first and second end effectors; and
 c) a surgical console comprising a processor constructed and arranged to execute an algorithm to position the positionable camera, wherein the processor is configured to define a location $P_L$ for the first end effector and a location $P_R$ for the second end effector, and to establish a Midpoint $P_L P_R$ between the first and second end effectors via the locations $P_L$ and $P_R$, and
 wherein the algorithm, when executed, positions the positionable camera such that the positionable camera is aligned with the Midpoint $P_L P_R$.

2. The robotic surgical system of claim 1, wherein the algorithm is configured to establish a camera reference frame and a robot reference frame, the camera reference frame having an origin, and wherein the algorithm, when executed, positions the positionable camera to align the origin of the camera reference frame with the Midpoint $P_L P_R$.

3. The robotic surgical system of claim 2, wherein the processor is configured to align the camera reference frame with the robot reference frame and re-position the positionable camera.

4. The robotic surgical system of claim 2, wherein the robot reference frame is established relative to the device body and is defined by orthogonal unit vectors $x_R$, $y_R$, and $z_R$.

5. The robotic surgical system of claim 2, wherein the camera reference frame is defined by orthogonal unit vectors $x_C$, $y_C$, and $z_R$.

6. The robotic surgical system of claim 1, wherein the positioning of the positionable camera to align with the Midpoint $P_L P_R$ comprises a damped motion.

7. The robotic surgical system of claim 6, wherein the damped motion of the positionable camera comprises a term proportional to a velocity of a tip of the positionable camera.

8. The robotic surgical system of claim 1, wherein the positionable camera comprises a tip configured to extend from a distal end of the camera lumen.

9. The robotic surgical system of claim 8, wherein the tip of the positionable camera is constructed and arranged to be capable of both pitch and yaw.

10. The robotic surgical system of claim 1, wherein the processor is further configured to execute a control algorithm for positioning of the first and second robotic surgical arms.

11. A robotic surgical system, comprising:
 a) a robotic surgical device comprising:
  i) a first robotic surgical arm operably coupled to a device body and comprising a first end effector;
  ii) a second robotic surgical arm operably coupled to the device body and comprising a second end effector; and
  iii) a camera lumen defined in the device body;
 b) a positionable camera constructed and arranged to provide views of the first end effector and the second end effector; and
 c) a surgical console comprising a processor constructed and arranged to execute a first algorithm to position the first and second robotic surgical arms, and a second algorithm to
  i) establish a camera reference frame having an origin,
  ii) establish a robot reference frame, and
  iii) position the positionable camera,
 wherein the processor is configured to define a location $P_L$ for the first end effector and a location $P_R$ for the second end effector, and to establish a Midpoint $P_L P_R$ between the first and second end effectors via the locations $P_L$ and $P_R$, and wherein the second algorithm positions the positionable camera such that the origin of the camera reference frame is aligned with the Midpoint $P_L P_R$.

12. The robotic surgical system of claim 11, wherein the processor is configured to align the camera reference frame with the robot reference frame and re-position the positionable camera.

13. The robotic surgical system of claim 11, wherein the positioning of the positionable camera to align the origin of the camera reference frame with the Midpoint $P_L P_R$ comprises a damped motion.

14. The robotic surgical system of claim 13, wherein the damped motion of the positionable camera comprises reducing a velocity of a tip of the positionable camera with a term proportional to the velocity of the tip.

15. The robotic surgical system of claim 11, wherein the positionable camera comprises a tip, and wherein the positionable camera is constructed and arranged to be inserted into the robotic surgical device such that the tip is configured to extend from the camera lumen to view the first and second end effectors.

16. The robotic surgical system of claim 15, wherein the tip of the positionable camera comprises an articulating tip constructed and arranged to be capable of both pitch and yaw.

17. The robotic surgical system of claim 16, wherein the articulating tip comprises a light source.

18. The robotic surgical system of claim 11, further comprising a robot clamp constructed and arranged to rotatably couple the robotic surgical device to a support arm.

* * * * *